United States Patent
Towfiq et al.

(10) Patent No.: US 8,323,201 B2
(45) Date of Patent: Dec. 4, 2012

(54) SYSTEM AND METHOD FOR THREE-DIMENSIONAL ULTRASOUND IMAGING

(75) Inventors: Farhad Towfiq, Dana Point, CA (US); Lawrence J. Busse, Fort Mitchell, KY (US); Stephen J. Douglas, Cary, NC (US)

(73) Assignee: Orison Corporation, Johnson City, TN (US)

( * ) Notice: Subject to any disclaimer, the term of this patent is extended or adjusted under 35 U.S.C. 154(b) by 688 days.

(21) Appl. No.: 12/186,967

(22) Filed: Aug. 6, 2008

(65) Prior Publication Data

US 2009/0043206 A1    Feb. 12, 2009

Related U.S. Application Data

(60) Provisional application No. 60/954,222, filed on Aug. 6, 2007, provisional application No. 60/986,770, filed on Nov. 9, 2007.

(51) Int. Cl.
*A61B 8/14* (2006.01)
*A61B 8/00* (2006.01)

(52) U.S. Cl. ........................ 600/459; 600/437

(58) Field of Classification Search .................. 600/437, 600/459; 367/138
See application file for complete search history.

(56) References Cited

U.S. PATENT DOCUMENTS

| | | |
|---|---|---|
| 3,480,002 A | 11/1969 | Flaherty et al. |
| 3,765,403 A | 10/1973 | Brenden |
| 3,964,296 A | 6/1976 | Matzuk |
| 4,341,222 A | 7/1982 | Gardineer et al. |
| 4,537,074 A | 8/1985 | Dietz |
| 4,545,385 A | 10/1985 | Pirschel |
| 4,888,746 A | 12/1989 | Wurster et al. |
| 5,042,492 A | 8/1991 | Dubut |
| 5,301,168 A | 4/1994 | Miller |
| 5,485,842 A | 1/1996 | Quistgaard |
| 5,535,751 A | 7/1996 | Raz |
| 5,677,491 A | 10/1997 | Ishrak et al. |
| 5,706,820 A | 1/1998 | Hossack et al. |

(Continued)

OTHER PUBLICATIONS

Cittadine, "Ultrasonic, Ultrasmall: Using MEMS and a newly developed ASIC for small-diameter pipe ultrasonic metering." Flow Control: The Magazine of Fluid Handling Systems, 27-30 (Nov./Dec. 2001).

(Continued)

*Primary Examiner* — Michael Rozanski
(74) *Attorney, Agent, or Firm* — Edwards Wildman Palmer LLP; Peter J. Manso

(57) ABSTRACT

Under one aspect, an ultrasound system for producing a representation of an object includes: a concave transducer array configured to transmit ultrasonic pulses into the object and to receive ultrasonic pulses from the object, the ultrasonic pulses from the object containing structural information about the object, each transducer in the array generating an output signal representative of a portion of the structural information about the object; a multi-focal lens structure for focusing the transmitted ultrasonic pulses; a multiplexing structure in operable communication with the concave transducer array and including logic for coupling the output signals from at least one pair of transducers in the concave transducer array; and a beamformer in operable communication with the multiplexing structure and including logic for constructing a representation of structural information about the object based on the coupled output signals from the multiplexing structure.

28 Claims, 18 Drawing Sheets

U.S. PATENT DOCUMENTS

| | | |
|---|---|---|
| 5,740,806 A | 4/1998 | Miller |
| 5,792,058 A | 8/1998 | Lee et al. |
| 5,797,845 A | 8/1998 | Barabash et al. |
| 5,810,742 A | 9/1998 | Pearlman |
| 5,840,032 A | 11/1998 | Hatfield et al. |
| 5,865,750 A | 2/1999 | Hatfield et al. |
| 5,882,309 A | 3/1999 | Chiao et al. |
| 5,897,501 A | 4/1999 | Wildes et al. |
| 5,956,292 A | 9/1999 | Bernstein |
| 6,102,857 A | 8/2000 | Kruger |
| 6,102,860 A | 8/2000 | Mooney |
| 6,117,080 A | 9/2000 | Schwartz |
| 6,183,419 B1 | 2/2001 | Wildes |
| 6,390,981 B1 | 5/2002 | Jago |
| 6,409,668 B1 | 6/2002 | Wollschlaeger |
| 6,478,739 B1 | 11/2002 | Hong |
| 6,511,426 B1 | 1/2003 | Hossack et al. |
| 6,511,433 B1 | 1/2003 | Benjamin |
| 6,618,206 B2 | 9/2003 | Tarakci et al. |
| 6,786,868 B2 | 9/2004 | Stotzka et al. |
| 6,899,696 B2 | 5/2005 | Morton et al. |
| 2002/0120195 A1 | 8/2002 | Hossack et al. |
| 2003/0007598 A1 | 1/2003 | Wang et al. |
| 2003/0076599 A1 | 4/2003 | Tarakci et al. |
| 2003/0085635 A1 | 5/2003 | Davidsen |
| 2004/0002435 A1 | 1/2004 | Petersen et al. |
| 2004/0002652 A1 | 1/2004 | Phelps et al. |
| 2004/0002656 A1 | 1/2004 | Sheljaskow et al. |
| 2004/0004906 A1 | 1/2004 | Vernet et al. |
| 2004/0044284 A1 | 3/2004 | Von Behren et al. |
| 2004/0122321 A1 | 6/2004 | Alexandru |
| 2004/0254464 A1 | 12/2004 | Stribling |
| 2005/0054958 A1 | 3/2005 | Hoffmann |
| 2006/0235300 A1 | 10/2006 | Weng et al. |

OTHER PUBLICATIONS

Ladabaum et al., "Surface Micromachined Capacitive Ultrasonic Transducers," IEEE Transactions on Ultrasonics, Ferroelectrics, and Frequency Control, vol. 45, No. 3. 10-26 (May 1998).

Microwaves101.com, "Phase Array Antennas," web page at http://www.microwaves101.com/encyclopedia/phasedarrays.cfm, 8 pages (printed on Jul. 19, 2007).

Oelze, "Ultrasound Sources: ECE 437," lecture slides. University of Illinois Urbana—Champaign USA, 56 pages (Spring 2007).

PCT International Search Report for International application No. PCT/US2008/009442, 2 pages (Oct. 22, 2008).

PCT Written Opinion of the International Searching Authority for International application No. PCT/US2008/009442, 7 pages (Oct. 7, 2008).

Ramamurthy et al., "Whitepaper ACUSON Sequoia Ultrasound Platform Compound Imaging Technologies," Siemens Medical Solutions USA, Inc., Ultrasound Division, Mountain View CA, 8 pages (2004).

Sensant Advanced Diagnostic Medical Imaging, "Silicon Ultrasound: Sensant's Breakthrough Transducers for Medical Imaging." web page at http://www.sensat.com/pro_advDiag.html, 2 pages (printed on May 27, 2003).

SonoSite, Inc., "SonoSite TITAN System Specifications," product brochure, 1 page (2003).

SonoSite, Inc., "Understanding Ultrasound: A Cornerstone of Visual Medicine and Diagnostics," tutorial paper on SonoSite web site, 4 pages (2003).

Supertex Inc., "HV2701 Low Charge Injection 16-Channel High Voltage Analog Switch with Bleed Resistors," product brochure, Sunnyvale CA USA. 8 pages (2007).

Thomenius, "Evolution of Ultrasound Beamformers," 1996 IEEE Ultrasonics Symposium 1615-1622 (1996).

Wikipedia.com, "Beamforming," web page at http://en.wikipedia.org/wiki/Beamformer, 4 pages (printed on Jul. 19, 2007).

Wikipedia.com, "Ultrasound," web page at http://en.wikipedia.org/wiki/Ultrasound, 9 pages (printed on Jul. 19, 2007).

SYSTEM AND METHOD FOR THREE-DIMENSIONAL ULTRASOUND IMAGING

RELATED APPLICATIONS

This application claims the benefit of U.S. Provisional Patent Application No. 60/954,222, filed Aug. 6, 2007 and entitled "System and Method for Three-Dimensional Ultrasound Imaging," the entire contents of which are incorporated by reference herein.

This application also claims the benefit of U.S. Provisional Patent Application No. 60/986,770, filed Nov. 9, 2007 and entitled "Freestanding Ultrasonic Breast Scanning System," the entire contents of which are incorporated by reference herein.

FIELD OF THE INVENTION

This application generally relates to ultrasonic imaging, and more particularly to medical three-dimensional ultrasound imaging systems.

BACKGROUND OF THE INVENTION

Timely diagnosis of potential ailments is perhaps the most effective tool available to modern physicians in their battle against serious illnesses. If discovered early enough, many of the deadliest illnesses and diseases pose little threat to a patient with proper treatment. To discover an illness, physicians typically perform a careful examination of a particular part of the human body, either by an invasive, or a non-invasive procedure. An example of an invasive procedure is the biopsy, in which a surgeon removes a sample of human tissue with a needle or a scalpel. Invasive procedures like the biopsy have inherent drawbacks, such as pain for the patient, and the need to heal the area from which the tissue sample was removed. Thankfully, technological and medical advances over the past fifty years have created a number of non-invasive diagnostic procedures.

Non-invasive diagnostic techniques such as Magnetic Resonance Imaging ("MRI"), Computer Tomography ("CAT" or "CT"), X-rays, Positron Emission Tomography ("PET") and Ultrasonography are widely used by physicians today. However, while non-invasive techniques are painless and do not require healing time, they may still pose certain dangers to the patient. For example, an unhealthy dose of X-ray radiation may lead to cancer. The strong magnetic fields produced by an MRI machine may also cause adverse health effects in the patient. In contrast with these devices, ultrasonography does not rely on electromagnetic waves or ionizing radiation. Ultrasound machines instead depend on mechanical vibrations to perform measurements.

Briefly, ultrasound machines include a transducer array, a beamformer, a processor, and a display. A transducer is a device that converts one type of energy to another type of energy. Ultrasound machines mostly use electroacoustic transducers, which convert electrical energy (voltage potential across the transducer) into mechanical energy (vibrations), and vice versa. The beamformer sets the phase delay and amplitude of each transducer element to enable dynamic focusing and beam steering. Where appropriate, a lens is mounted on the transducer array to focus the transmitted pulses and received echoes. In operation, the transducer array sends out a number of pulses directed toward the anatomical area of a patient to be imaged, and after a certain propagation delay receives echoes that were reflected back by the patient's anatomy. The received signal can then be presented on a display for immediate examination or recorded for a later review.

Over time, the industry has developed a commonly understood terminology for describing various components of an ultrasound machine. The various combinations of transducer arrays and multiplexers were in particular need of a common term, due to the different goals and performance attributable to each combination. While terminology used by the industry is generally agreed upon, certain variations exist, mostly regarding the multiplexing structures that connect transducer arrays to the beamformer.

The terms are generally understood by persons in the art as follows:
  1D arrays have a fixed elevation aperture and are focused at a static range.
  1.5D arrays have a variable elevation aperture, and either static or dynamic focusing (Industry terminology for this category differs. For example, General Electric (GE) splits these arrays into two categories: 1.25D and 1.5D. In GE terms, a 1.25D array provides for variable elevation aperture, but its focusing remains static. However, a 1.5D array, in GE terms, has a dynamically variable aperture, shading, and focusing, all which are symmetric about the elevational centerline of the array. A GE article titled "Elevation Performance of 1.25D and 1.5D Transducer Arrays" by Wildes et al., the entire contents of which are incorporated herein by reference, provides an overview of various linear transducer arrays.).
  2D arrays permit focusing and steering in both azimuthal and elevational directions, with comparable results.

Regarding actual ultrasound machines, ordinary hand-held and stationary scanners such as the ones depicted in FIGS. 1A and 1B have been used since the 1970s. As technology progressed, so did the quality of images provided by ultrasound machines. Phased arrays, such as the 1D array pictured in FIG. 2A, have drastically improved lateral and axial resolutions of ultrasound machines. Axial resolution is the minimum separation required between reflecting objects stationed in the path of the ultrasonic pulse. If two reflecting objects are too close together, the received echoes are also too close together, appearing as if they were reflected by a single object. Lateral resolution is the minimum separation required between reflecting objects in the direction perpendicular to the path of the ultrasonic pulse. While 1D phased or linear arrays improve lateral and axial resolutions, their elevation performance is controlled by using a simple lens, which leads to a more uniform slice thickness but only permits elevation focusing at a single focal distance, with a depth of focus that depends on the elevation aperture. The elevation aperture must be proportional to the focal distance, and at the same time narrow enough to provide a sufficient depth of focus. However, a narrower elevation aperture provides less effective focusing, and hence results in a lower lateral resolution.

More recent developments, such as the 1.5D array depicted in FIG. 2B, have improved elevation slice-thickness performance both in the near- and far-fields, while still using only a single beamformer for both azimuthal and elevation focusing. However, these kinds of arrays suffer from limited penetration depth, the possibility of beam-splitting caused by the shape of the lens, and also by their cumbersome and slow multiplexing structures.

Lenses with a cross-section shown in FIG. 2b, are prone to a phenomenon known as beam-splitting, because their cross-sectional depth does not take into account a wave's propagation time. For example, the lens's center row is the first to receive and quickly pass the echo through to the multiplexer.

However, by the time the lens's outer rows receive and pass through their own parts of the echo, the time-frame has shifted, and it is unclear which echoes are being passed through. Thus, the beam is actually "split" into components which might not be received simultaneously by the beamformer.

Another downside of the 1.5D array depicted in FIG. 2b is its slow multiplexing structure, or more accurately its two multiplexing structures. Such an array, described in U.S. Pat. No. 5,882,309 to Chiao et al., the entire contents of which are incorporated herein by reference, actually has two multiplexers. One multiplexer controls elevation aperture growth, while the other controls azimuthal aperture growth. This results in very slow scanning, as the two multiplexers cannot be switched independently of one another.

Convex 1D arrays, such as the one depicted in FIG. 3, suffer from a very limited penetration depth and lower resolutions because their geometry requires smaller elements to sustain the same f-number at greater depths.

Turning to three-dimensional (3D) imaging, performance in elevation focusing, depth of penetration and high resolution become very important, particularly in the medical field. When using ordinary ultrasound scanners, like the one depicted in FIG. 1A, physicians and ultrasound specialists receive one or more two-dimensional images in the azimuthal plane. As mentioned earlier, modern transducer arrays capable of dynamic focusing provide a large azimuthal aperture, leading to high quality two-dimensional images. In the medical field, the same resolution quality would also be expected of 3D images. Thus, elevation focusing performance of the 2D image slices making up the 3D image becomes very important. In addition, an automated 3D ultrasound imaging machine should also provide high resolution quality at greater depths, since there is no operator to make needed adjustments, as there would be with a manual ultrasound scanner. Accordingly, there is a need to provide an ultrasound system for three-dimensional imaging, without the drawbacks associated with the prior art. To this end, it is desirable to provide a system capable of an increased penetration depth, shorter imaging time, more efficient multiplexing structure, and greater flexibility in azimuthal and elevational focusing.

SUMMARY OF THE INVENTION

Under one aspect, an ultrasound system for producing a representation of an object includes: a concave transducer array configured to transmit ultrasonic pulses into the object and to receive ultrasonic pulses from the object, the ultrasonic pulses from the object containing structural information about the object, each transducer in the array generating an output signal representative of a portion of the structural information about the object; a multi-focal lens structure for focusing the transmitted ultrasonic pulses; a multiplexing structure in operable communication with the concave transducer array and including logic for coupling the output signals from at least one pair of transducers in the concave transducer array; and a beamformer in operable communication with the multiplexing structure and including logic for constructing a representation of structural information about the object based on the coupled output signals from the multiplexing structure.

In some embodiments, the concave transducer array comprises multiple rows of transducers. In some embodiments, the logic of the multiplexing structure includes instructions for varying at least one of a depth to which the ultrasonic pulses penetrate the object and an f-number of the array by uncoupling a subset of the transducers from the beamformer. Some embodiments further include a dome configured to accept the object, wherein the concave transducer array is mounted over a slit in the dome. Some embodiments further include a motor for rotating the concave transducer array about an axis of the dome, wherein the logic of the beamformer is configured to create image slices of the object located inside the dome as the motor rotates the array. Some embodiments further include logic for assembling a three-dimensional representation of the object located inside the dome by combining the stored image slices. In some embodiments, at least one of the multiplexing structure and the beamformer is mounted on the dome. Some embodiments further include a probe housing, wherein the dome is constructed and arranged within the housing such that the object can be imaged without compression. In some embodiments, the object is a breast.

Under another aspect, a method of producing a representation of an object includes: transmitting ultrasonic pulses into the object with a concave transducer array; focusing the ultrasonic pulses with a multi-focal lens structure coupled to the array; receiving ultrasonic pulses from the object, the received ultrasonic pulses containing structural information about the object; generating a plurality of output signals, each output signal representative of a portion of the structural information about the object; multiplexing a subset of the output signals; and obtaining a representation of structural information about the object based on the multiplexed subset of output signals.

Some embodiments further include receiving ultrasonic pulses from a variety of angles about the object, obtaining image slices of the object based on the received ultrasonic pulses, and creating a three-dimensional rendering of the object based on the image slices.

Under another aspect, a concave ultrasonic transducer array includes a plurality of curvilinear transducer rows, each transducer row comprising at least one ultrasonic transducer element; and a concave multi-focus lens coupled to the ultrasonic transducer elements.

In some embodiments, the concave multi-focus lens comprises a plurality of lens rows, one lens row coupled to each curvilinear transducer row. In some embodiments, some of the lens rows have at least one of a different dimension and a different focal length than other of the lens rows. In some embodiments, at least some of the transducer rows have a different dimension than other of the transducer rows. In some embodiments, each row comprises between 100 and 1000 transducer elements. In some embodiments, each row comprises between 300 and 600 transducer elements.

Under another aspect, a concave multi-focus acoustic lens includes a plurality of concave rows, wherein rows symmetric in elevation along an azimuthal centerline of the lens have the same focal points as each other, and wherein at least a subset of the rows are offset from other rows in a range direction.

In some embodiments, at least a subset of the rows have a different lateral dimension than other of the rows. In some embodiments, the lens is made of a material having a speed of sound of less than 1.5 mm/µs. In some embodiments, the material comprises one of silicone and urethane.

Under another aspect, a method of multiplexing signals from transducer elements in a concave transducer array includes: turning on rows of transducer elements in the concave transducer array based on a desired elevational beam performance; turning on columns of transducer elements in the concave transducer array based on a desired azimuthal beam performance; and connecting the turned on rows and columns to a beamformer.

DETAILED DESCRIPTION OF THE INVENTION

Figure 4:
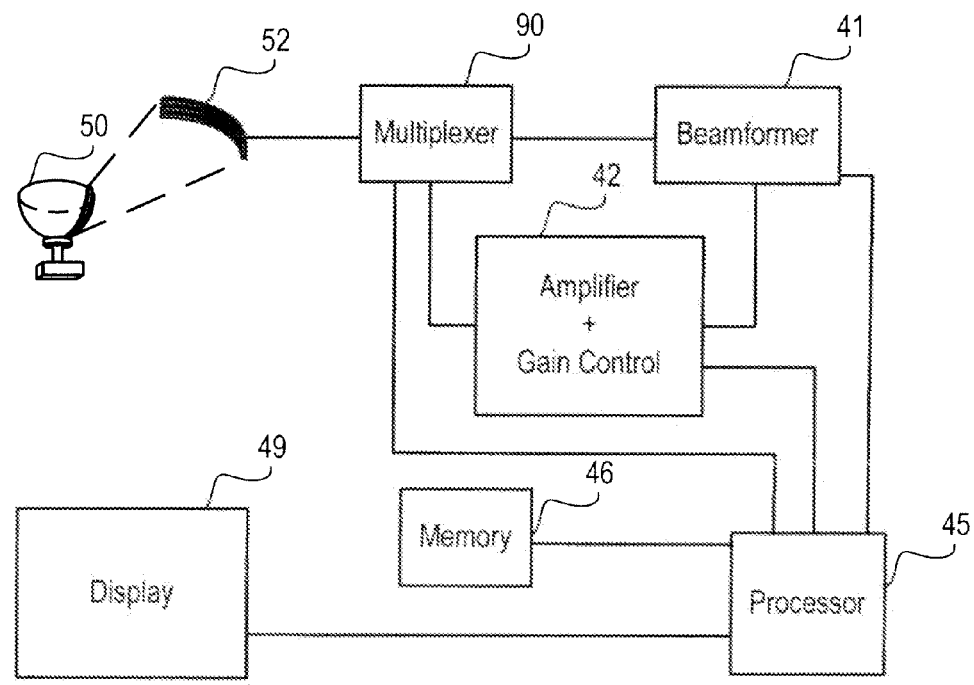
FIG. 4 is a block diagram of an ultrasound imaging system, according to some embodiments.

FIGS. 4-12 illustrate some embodiments of a 3D ultrasound imaging system 40. FIG. 4 illustrates a high-level overview of the components of system 40. System 40 includes a dome 50, a concave transducer array 52, a multiplexing structure 90 attached to the transducer array 52, a beamformer 41, an amplifier and gain control 42, a processor 45 with memory 46, and a display 49. The beamformer 41, multiplexer 90, amplifier and gain control 42, and processor 45 are all coupled to one another.

To create a 3D image of a particular part of human anatomy, the operator positions the part of human anatomy to be imaged inside the imaging dome 50. The system 40 can be used to image almost any part of the human body, depending on the size of the dome. For example, a shoulder, breast, wrist, ankle, elbow, or other parts of human anatomy can be positioned inside the dome. As will be understood by those of ordinary skill in the art, this can be accomplished by a variety of methods. One approach is to mount at least a portion of the ultrasonic system 40 on a mechanical arm with multiple degrees of freedom of rotation, which in some embodiments allows the operator to place the dome in a preferred position, similar to hospital x-ray machines. Another approach is to place the patient in a position where the body part to be imaged is placed inside the dome. In the second approach, the ultrasound machine itself makes minimal movement, and it is the patient who is being properly positioned by the operator.

Figure 5:
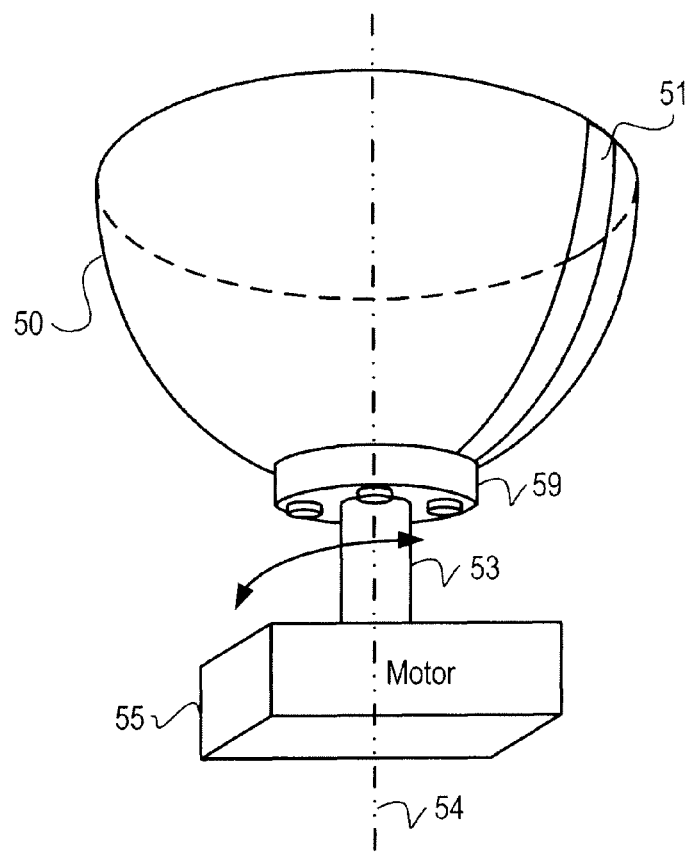
FIG. 5 is an illustration of a dome for ultrasonic scanning mounted to a stepper motor, according to some embodiments.
Figure 6:
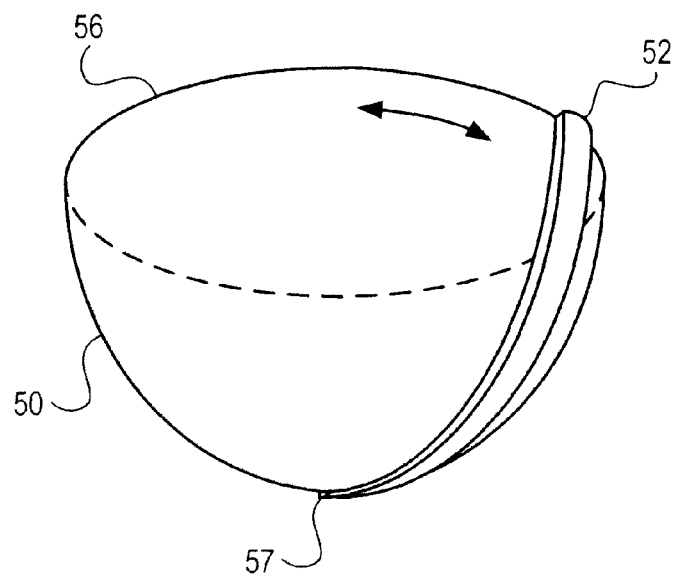
FIG. 6 is an illustration of a concave ultrasonic transducer array mounted on a dome, according to some embodiments.

Once the desired object has been placed inside the dome, the operator selects a desired mode of operation, and activates the system 40. As illustrated in FIGS. 5 and 6, a concave 1.5D transducer 52 array is mounted on the dome 50, and rotated with the dome 50 along the main axis of the dome by a motor 55. In some embodiments, the dome 50 and array 52 are be able to rotate 360°. However, other, less exhaustive imaging regimes are possible. At the end of the rotation, the system 40 combines all of the two-dimensional image slices obtained during the scan to create a three-dimensional image of the object inside the dome 50, and the image is displayed on display 49 to the operator. The individual components of the system 40 are discussed next.

Dome

FIG. 5 is an illustration of one embodiment of dome 50. Dome 50 has an axis 54 running from the dome's pole to the center of the circle or oval created by the dome's edge 56. The dome is a conventional dome composed of a light-weight material, such as plastic. Dome 50 contains a slit 51, through which transducer array 52 transmits and receives ultrasonic pulses. To facilitate the propagation of ultrasonic pulses between array 52 and the object placed inside the dome for imaging, the inside of the dome is filled with a coupling fluid made of an acoustically conductive material, such as water, commercial gel, or a unique hydrogel. For examples of a suitable coupling fluid, see PCT Patent Application No. PCT/US08/08414, filed Jul. 9, 2008 and entitled "Ultrasound Coupling Material," the entire contents of which are incorporated herein by reference. Transducer array 52 is attached to the dome 50 as illustrated in FIG. 6. Motor 55 is attached to dome 50 for the purpose of rotating the dome around central axis 54. The rotation can be accomplished via shaft 53, which is connected to both dome 50 and motor 55. Motor 55 should be capable of rotating drive shaft 53 a full 360°, preferably in increments of 0.45°, 0.9°, or 1.8°. In some embodiments, motor 55 is a stepper motor, however in other embodiments it can also be a servomotor, or any other motor capable of performing rotation in small, measurable steps.

As shown in FIG. 6, in some embodiments transducer array 52 is mounted on dome 50 such that each transducer element has an unobstructed view of the inside of the dome through slit 51. For this to be possible, slit 51 must be large enough to accommodate the entire array 52. Slit 51 should also be of substantially similar curvature to array 52 for proper focusing, as will be further discussed below. Since in some embodiments, dome 50 is filled with coupling fluid, the transducer array can be mounted on the dome in a manner that inhibits or prevents the coupling fluid from leaking out through slit 51. This can be accomplished by making the surface area of transducer array 50 equal to that of slit 51, and filling up any remaining space between the edges of the slit and the array with a sealant. The sealant can also serve as glue to hold the array inside slit 51. In another embodiment, a rubber spacer can be placed between the transducer array and the edges of slit 51, shaped to both hold the array in place and prevent the coupling fluid from leaking out.

It will be understood by those skilled in the art that the curvature and size of dome 50 and slit 51 may vary depending on specific imaging requirements. In many embodiments, dome 50 is large enough to encompass the object that will be imaged. In one embodiment, dome 50 and transducer array 52 are mounted on an immobile support structure, such as a hospital bed or a wall. In this embodiment, the dome and array are still capable of revolving, e.g., by 360°, but the entire system is stationary and cannot be positioned with respect to the patient; rather, it is the patient who has to be properly positioned. In another embodiment, dome 50 and transducer array 52 are attached to a movable mechanical arm with multiple degrees of freedom, so that the patient can sit or lie in a comfortable position while the operator conveniently places the dome over the body party to be imaged. In yet another embodiment, dome 50 and transducer array 52 are mounted on a wheeled platform, so that it can be transferred from room to room, or closer to a patient. A person of ordinary skill in the art will recognize that multiple combinations of these embodiments are possible. For examples of additional embodiments, see below.

While in some embodiments the dome is securely attached to base 59, as well as the stepper motor and rotating assembly, the dome can also be configured so as to be removable so that it could be sanitized and washed after a scan. To this end, the dome can be made of a non-corrosive material. e.g., a material that is be safe for contact with human skin.

Array

Figure 7A:
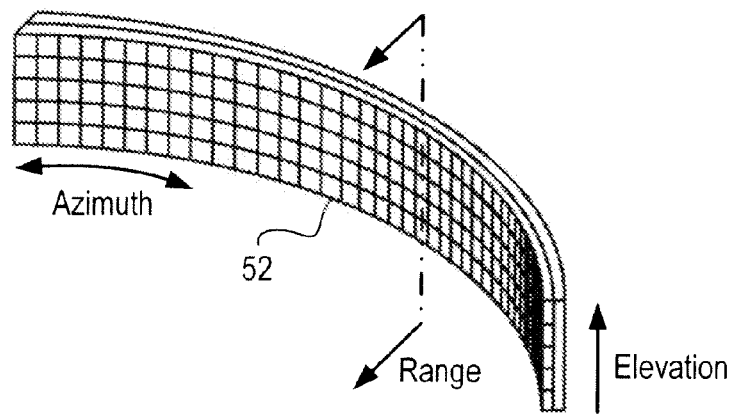
FIG. 7A is an isometric view of a concave ultrasonic transducer array, according to some embodiments.

As previously discussed, a concave transducer array 52 is mounted on top of slit 51 in dome 50 (FIG. 6). FIG. 7A provides a closer illustration of the array, according to some embodiments. Traditionally, the direction in which sound pulses are transmitted and received from is called the range, the direction above or below the center transducer row is called the elevation, and the direction along the length of a transducer row is called the azimuth.

An ultrasonic transducer array includes a plurality of transducer elements. Generally speaking, a transducer is a device that converts one form of energy to another form of energy. Transducers used in ultrasound machines can be described as electroacoustic transducers because they convert a voltage potential applied across the transducer into a sound wave, and vice versa. When a transducer element is being designed, a single surface is identified, and later manufactured, as the transmit/receive surface of the transducer element. Thus, when a sound wave impacts on the transmit/receive surface, thereby applying pressure on the surface, the transducer element creates a voltage potential that is measured and processed by the ultrasound machine. Heading in the other direction, when a voltage signal with a proper resonant frequency is applied to the transducer element, the transmit/receive surface begins to vibrate, thereby applying pressure on an adjacent medium, which in turn creates a traveling ultrasound wave. However, once the voltage signal is discontinued, the transducer does not stop vibrating instantaneously, and it takes a certain amount of time for the vibrations to settle to negligible levels. To dampen the vibrations, backing material 79 is often added to the surface of the element opposite the transmit/receive surface (e.g., as is illustrated in FIG. 7C). One or more matching layers 78 with a width of $$\frac{1}{4}\lambda$$

($\lambda$ being the wavelength of the transmitted pulse) can also be added to the transmit/receive surface of the transducer. The backing and matching layers can be helpful in implementing rapid transmit/receive sequences, since these layers permit a vibrating transducer to settle down more quickly.

It is well known in the art that an array with multiple transducer elements provides the ability to enhance axial and lateral resolution by focusing the beam. Adding rows of elements to the array also improves the system's elevational performance. However, where increased beam penetration is desired, linear arrays fall short. A linear array may decrease the transmission frequency to increase penetration depth, however this will result in a lower resolution. A much better approach to improving penetration performance is to change the geometry of the array.

Some terminology should be addressed before turning to the geometry of the array provided herein. As used in the art, a "surface normal," or simply a "normal," is a three-dimensional vector which is perpendicular to that surface. The "angle of incidence," or "incident angle," is the angle between a beam incident on a surface, and the normal at the point of incidence. The "acceptance angle," is the minimum angle between a receiving surface and a beam incident on the receiving surface, at which the receiving surface absorbs at least some of the beam's energy. In transducers, smaller angles of incidence result in more power being absorbed by the receiving surface of the transducer. In other words, to maximize the amount of received power, the beam has to be perpendicular to the receiving surface of the transducer.

Keeping the above in mind, and turning to array geometry, it follows that in a flat linear array, the transducer elements located directly in front of a returning echo receive most of the echo's power. However, some transducer elements located further away from the normal also receive a portion of the echo, albeit at lower power, since the angle of incidence increases for those transducer elements. Naturally, it is desirable to capture as much of a returning echo as possible. In a flat transducer array, this means activating more elements to increase the available receive area. However, a concave ultrasound transducer array, such as the one depicted in FIG. 7A, is naturally shaped to receive more power from a returning echo than a linear array. The concave array's natural curvature decreases the angles of incidence on its outer elements (those elements being further away from the normal). With lower angles of incidence, outer elements of a concave array receive more power than the corresponding outer elements of a flat array. Just as importantly, by virtue of the lesser incidence angles experienced by its outer elements, a concave array has more outer elements available to receive echoes from greater depths than a flat array. This results in greater penetration depth by a concave array than a flat array. At the same time, a multi-row concave array retains all of the benefits usually associated with such arrays, such as axial, lateral, and elevational resolution performance. The dimensions of array elements illustrated as small squares in FIG. 7A do not correspond to their actual size, or proportion; rather the figure is intended to illustrate the transmit/receive area of the array.

Figure 7B:
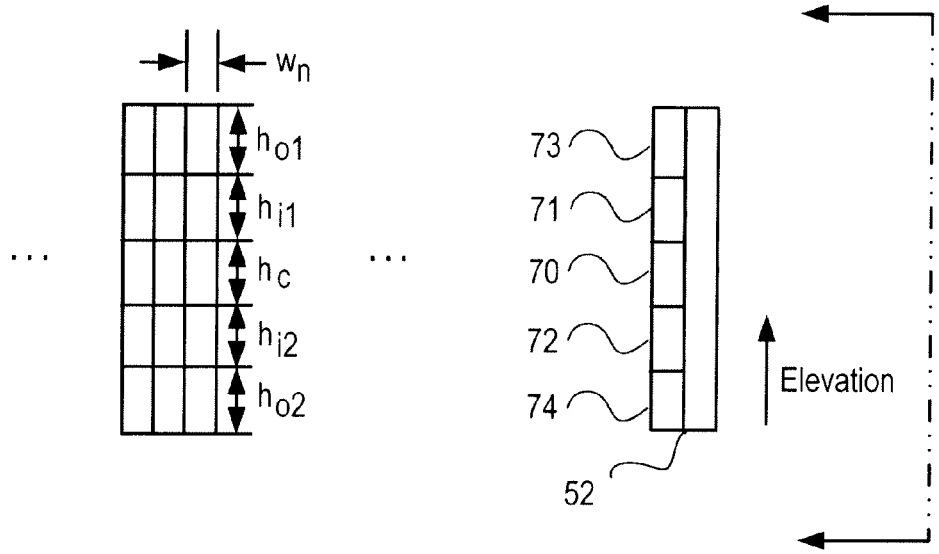
FIG. 7B is an enlarged view of the transmit/receive surface of a concave transducer array and a cross-sectional view of a concave ultrasonic transducer array, according to some embodiments.
Figure 7C:
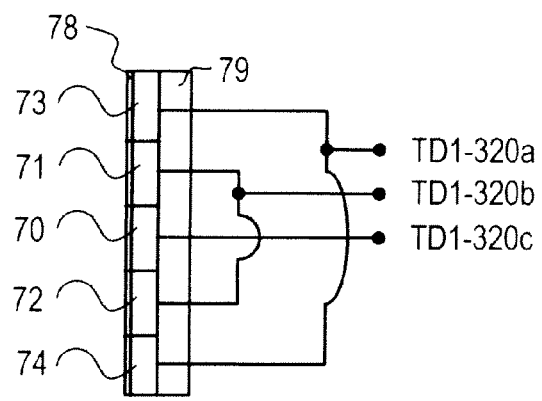
FIG. 7C is a cross-sectional view of a concave ultrasonic transducer array with signal connections, according to some embodiments.

As can be seen from a cross-sectional view of the array provided in FIG. 7B, the array includes a plurality of rows, with each row including a plurality of transducer elements. In the illustrated embodiment, the array has 5 rows: center row 70, inner rows 71 and 72, and outer rows 73 and 74. As illustrated in FIG. 7B, the center row has elevational height $h_c$, inner rows 71 and 72 have heights of $h_{i1}$ and $h_{i2}$, respectively, and outer rows 73 and 74 have heights of $h_{o1}$ and $h_{o2}$ respectively. Each of the elements has a width of $w_n$. In the some embodiments, each of the rows has 320 elements. In another embodiment, the array has 3 rows with 480 elements each. It will be understood by those of ordinary skill in the art that many combinations of row and element arrangements and numbers are possible. For example, in some embodiments there are between 2 and 10 rows, e.g., between 3 and 8 rows, between 4 and 7 rows, or 5-6 rows. Each row can have, e.g., between 50 and 1000 elements, between 100 and 800 elements, between 200 and 600 elements, or between 300 and 500 elements.

The overall curvature and length of the array 52 depends on multiple factors, some of which are the curvature and dimensions of the dome. If, as in the illustrated embodiment, the array stretches from edge 56 of the dome to pole 57 of the dome (FIG. 6), then the curvature of the array can be selected to match the curvature of the dome. In one embodiment, the array has an 85 mm radius of curvature. Naturally, the array does not have to stretch from the edge of the dome to its pole, particularly if electronic beam steering is applied. Steering the beam can be accomplished by varying the delay with which adjacent transducers transmit and receive their pulses. For example, varying the delay of each pulse transmission also changes the phase of each transmitted pulse, and if the delay is increased linearly from element to element, a wavefront traveling away from the transmit/receive surface of the array at an angle is ultimately created. If the delays have been carefully coordinated, the transmitted wavefront, and the received echoes can be processed at an angle. It is therefore possible to have an array that does not stretch the entirety of the surface between an edge of a dome and its pole, and still be able to cover significant portions of the dome's volume.

Another application of delay circuitry is that of dynamic focusing. The focal point of an array depends on the size of the transmit/receive area, also known as the aperture. A larger aperture has a focal point that is located further away from the array than the focal point of a smaller aperture. It follows, that multi-element transducer arrays are perfectly designed to change their own focal point, by virtue of adding or subtracting active transducer elements. FIG. 8D is an illustration of dynamic focusing in the azimuthal plane performed by a concave array 52 in accordance with the illustrated embodiment. FIG. 8D shows that a beam emitted by a small number of active array elements, i.e. the 4 elements located close to the center of the array 52, focuses around the nearest point of the four possible. When more elements are added to the array, the focal point moves further away from the transmit/receive surface. By dynamically varying the aperture of the array, and simultaneously changing the focal point, the system can obtain the desired focusing performance. In practice, this results in obtaining high resolution echoes from many locations along the beam path. In some embodiments, the system 40 has three to seven such focal zones per scan line. Since it takes time to transmit a pulse and receive an echo from any focal distance, it will be understood that having additional focal zones can increases the amount of time needed to complete the scan line. Thus, if the system is set to three focal zones per scan line, it can complete the scan faster than if it were set to seven focal zones per scan line. The details of changing the aperture of the array are discussed in the multiplexing section below.

As is generally accepted in the industry, spacing between the elements of a transducer row may be reduced to reduce or avoid gaps in coverage. In the illustrated embodiment, the center-to-center spacing between transducer elements in a row, also known as the "pitch," is 0.4 mm. In some embodiments, to enhance penetration and resolution, the transducer elements are designed to be excited at 6.5 MHz to 7.5 MHz. It will be understood by those of ordinary skill in the art that other frequencies and a different pitch can also produce acceptable results. For example, the transducer elements can transmit a pulse when excited by a frequency of between 4 MHz and 9 MHz.

As previously mentioned, having multiple rows in an array 52 allows the system to change the transmit/receive aperture by turning on multiple rows simultaneously. The rows do not have to be of equal height. One exemplary embodiment includes five rows, in which the center row 70 has a height $h_c$ of 2.8 mm, inner rows 71 and 72 have a height $h_{i1}$, $h_{i2}$ of 1.4 mm each, and outer rows 73 and 74 have a height $h_{o1}$, $h_{o2}$ of 3.2 mm each. Changing the height of a row can affect the focal point of an active array, and also change the elevation beam performance. FIG. 8E is an illustration of elevation beam performance. Similarly to FIG. 8D, which shows azimuthal focusing, FIG. 8E shows that an increased elevation aperture also moves the focal point of the array 52 further away from the transmit/receive surface. Since a 1.5D array does not have as many rows as it has elements per row (also called columns), it follows that the elevational focusing performance for a 1.5D array is not as good as its azimuthal focusing performance. In one embodiment of 5 rows, the array has 3 elevational focal zones depicted in FIG. 8E.

Turning to the signal pathways used by the array 52, each transducer element has an electrical connection. However, instead of connecting every element of every row to the multiplexer 90, significant savings can be accomplished by treating multiple elements of the array 52 in the elevational direction as a single element. In some embodiments, this is accomplished by tying together signal connections of each transducer element located in inner row 71 with a corresponding transducer element located in inner row 72. The same is done with elements located in outer rows 73 and 74, in accordance with FIG. 7C. Note that none of the elements located in the same row are fused together. This means that for an array of 5 rows with 320 elements in each row, there are a total of 320×3 signal connections leaving the array. It will be understood by those of ordinary skill in the art that the nature of the signal pathways themselves can vary. Once the transducer has converted a sound wave into an electrical signal, it can then be transmitted by ordinary wire, cable, or fiber to the multiplexer 90 and beamformer 41. Longer connections, however, result in signal attenuation, and it is preferable to place the multiplexer 90 and beamformer 41 as close to the array as possible. The multiplexing structure 90 itself is discussed below.

Lens

It is well known in the art that a beam emitted by a focused ultrasound transducer converges on a focal point, and rapidly diverges as it moves past the transducer's focal point. However, the width of the beam at the focal point and elsewhere, both in the azimuthal and elevation directions, depends, among other factors, on the aperture of the transducer, the frequency of the pulse, and whether a lens is applied. This phenomenon creates many hurdles in the ultrasonic imaging process. For example, a beam that is too wide at its focal point will cover multiple reflecting objects, and therefore the lateral resolution will suffer. Following the same concept, an unfocused beam's performance will also suffer in the elevation direction. Therefore, it becomes necessary to focus the ultrasonic transducer array. As described earlier, changing aperture and time delays permits focusing of the array in the azimuthal plane. However, having a limited number of rows hampers the ability to focus the array elevationally. In response to this problem, focusing lenses are applied.

Figure 8A:
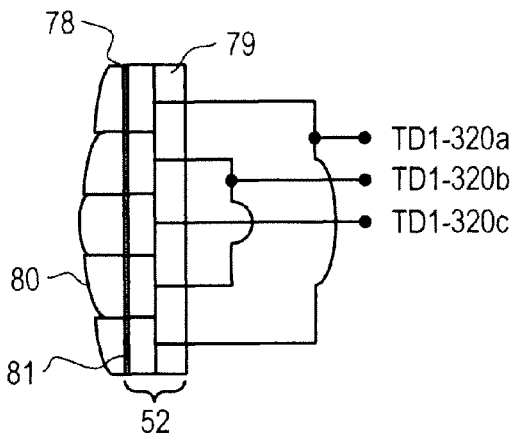
FIG. 8A is a cross-sectional view of a concave ultrasonic transducer array with a concave focusing lens, according to some embodiments.
Figure 8B:
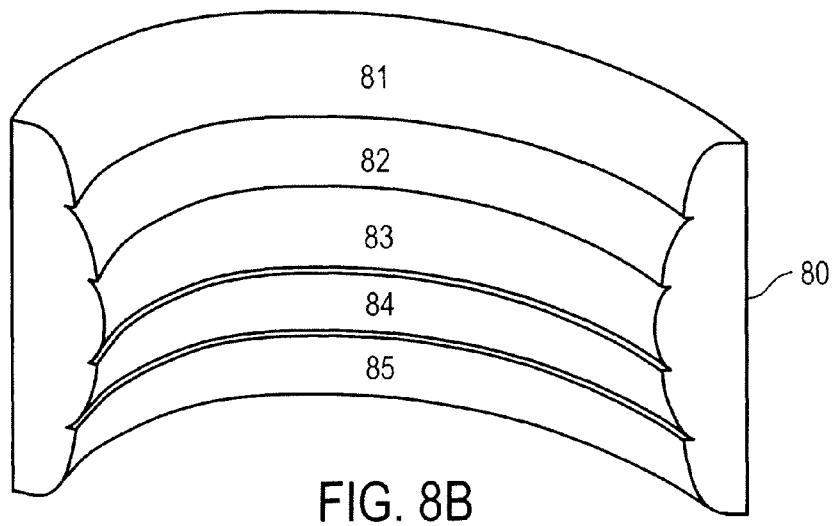
FIG. 8B is an isometric view of a concave focusing lens, according to some embodiments.
Figure 8C:
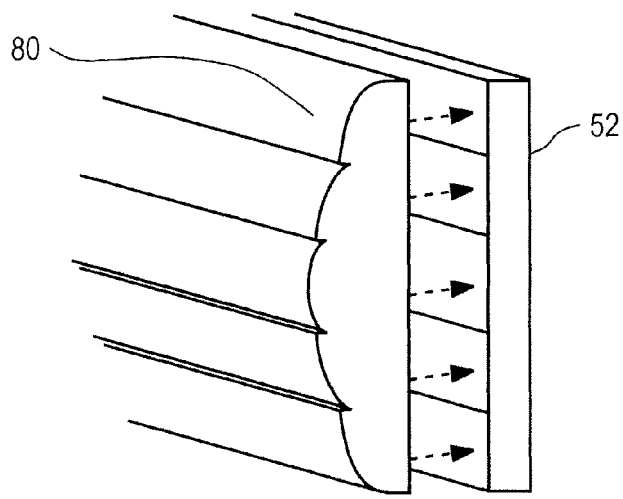
FIG. 8C is an illustration of the concave focusing lens being mounted on the transmit/receive surface of the concave transducer array, according to some embodiments.
Figure 8D:
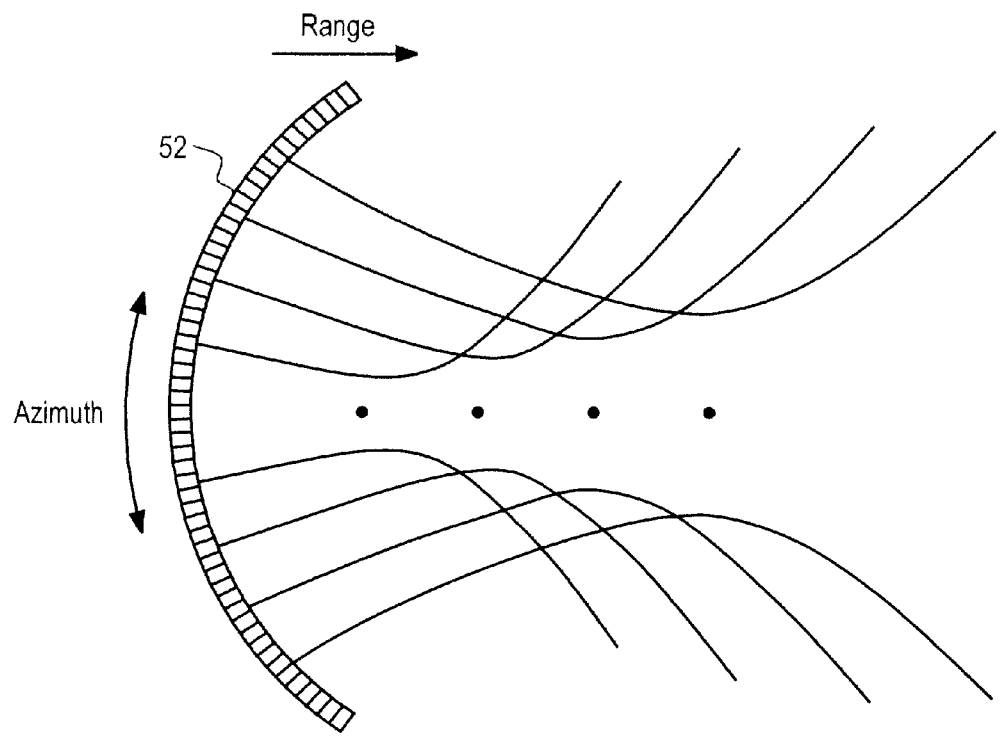
FIG. 8D is a diagram of the focal zones for a concave transducer array in the image plane, according to some embodiments.
Figure 8E:
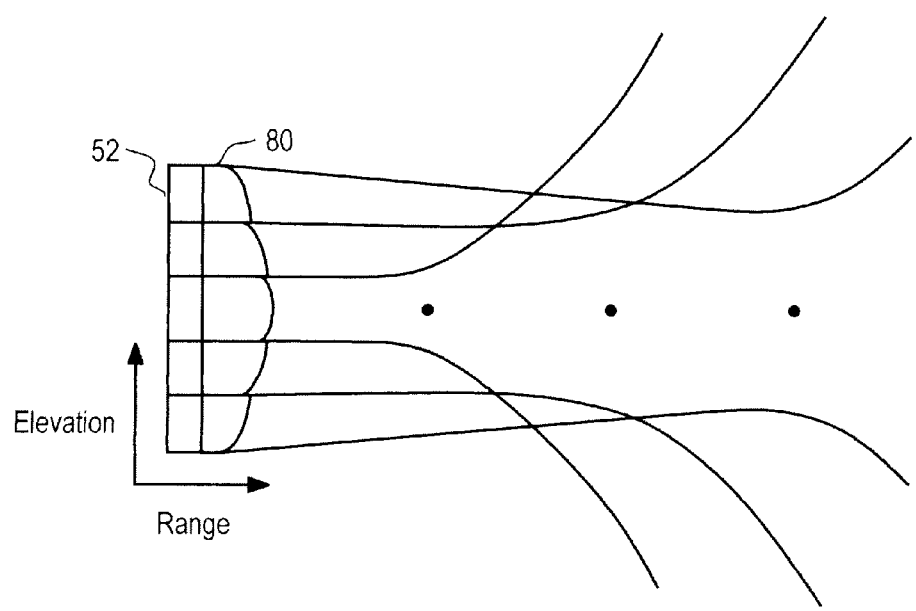
FIG. 8E is a diagram of the focal zones for a concave transducer array in the elevation versus range plane, otherwise known as the elevation beam performance, according to some embodiments.

One approach to focusing an ultrasonic transducer array is to use an acoustic lens, such as lens 80 depicted in FIGS. 8A-8F. In the illustrated embodiments, a concave lens is used to cover the entire transmit/receive area of the concave transducer array 52 to focus the beam in the elevation direction. An ordinary homogeneous lens with uniform curvature and a single index of refraction has a single fixed focal point. However, a multi-row array with a single focal point would lose much of it appeal, namely the ability to vary the transmit/receive aperture of the array. To this end, a multi-focal compound lens improves the ability to focus the transducer array at desired locations along the path of the beam as the array's elevational aperture varies. FIG. 8A shows a cross-section of the array 52 with an attached multi-focus lens 80. An isometric view of the concave multi-focus lens 80 can be seen in FIG. 8B.

As illustrated in FIG. 8B, multi-focus lens 80 includes multiple lens sections (also called lens rows) 81, 82, 83, 84, and 85, with each section being similar in size to the transducer row being focused (here, rows 73, 71, 70, 72, and 74, respectively). In the embodiment illustrated in FIG. 8C, each section of multi-focus lens 80 is elevationally and azimuthally aligned with the transducer row that it covers. In other words, the entire transmit/receive area of a transducer row is covered by a row of the lens 80, in some embodiments.

In some embodiments, multi-focus lens 80 should be made of material such as Silicone or Urethane, in which the speed of propagation for a sound wave is slower than $$1.5 \frac{mm}{\mu s}.$$

As mentioned earlier, the dome 50 can be filled with a coupling fluid or gel. To improve performance, the material of which the lens 80 is composed matches the acoustic impedance of the coupling fluid. Lens 80 can be attached to transducer array 52 by glue or a molding process, as illustrated in FIG. 8C. Line 81 in FIG. 8A shows that in many embodiments, there is substantially no gap between the transducer array 52 and the lens 80, after the two are mated together.

Figure 8F:
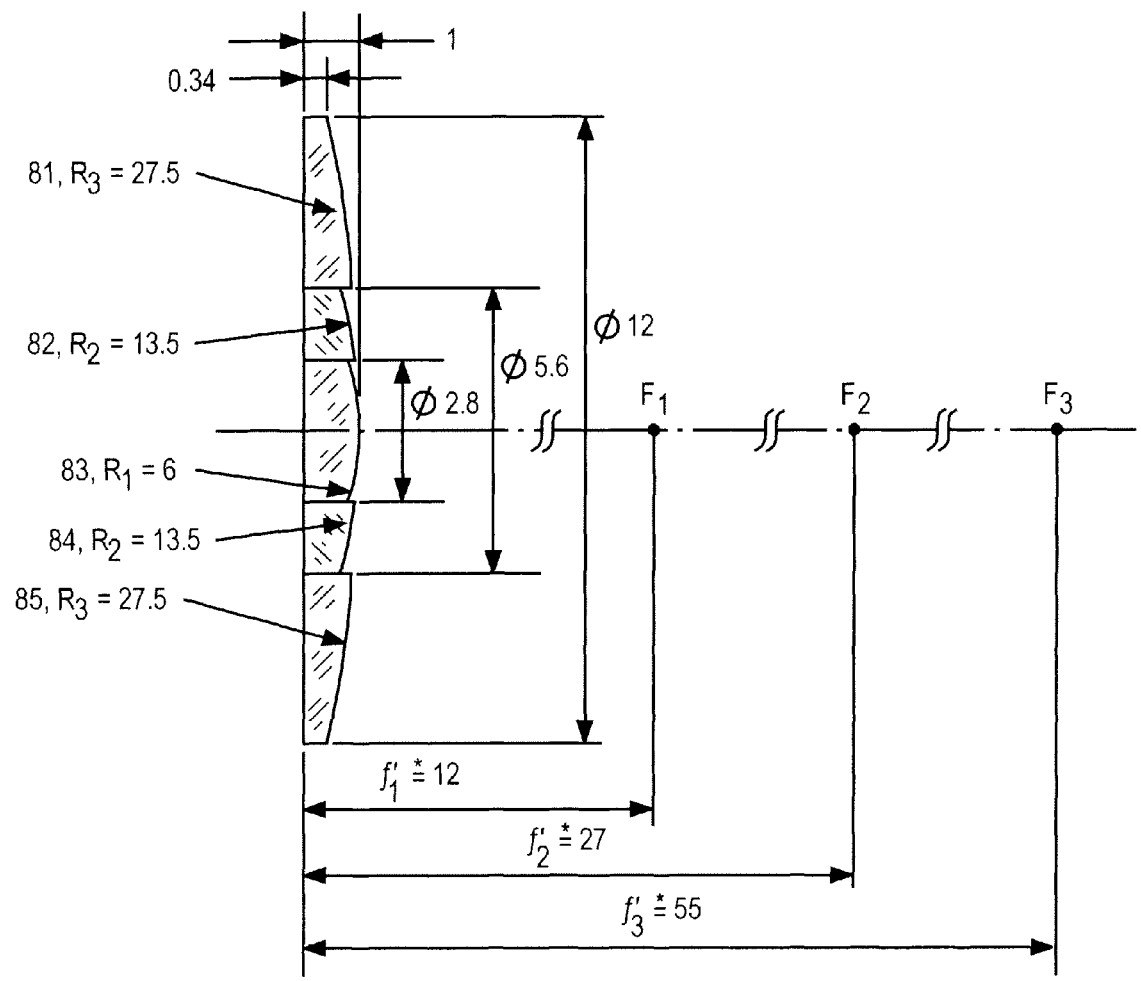
FIG. 8F is a detailed cross-sectional view of an embodiment of the concave focusing lens in the elevation versus range plane, according to some embodiments.

In the illustrated embodiment, each lens section (or row) has a constant curvature when viewed from a cross-sectional vantage point, seen in FIG. 8F. The center row 83 has the smallest radius (greatest curvature) compared to other rows 81, 82, 84, 85. As rows get farther away from the center row 83, their radius increases and their curvature decreases. It should be noted that the curvature being discussed here is the curvature of each lens row as seen on the elevation versus range plane (shown in FIG. 8F), and not the curvature of the entire lens illustrated in FIG. 8B. The curvature of the entire lens depends on the curvature of the dome and the array illustrated in FIGS. 5A, 5B and discussed above.

In the embodiment illustrated in FIG. 8F, center row 83 has a cross-sectional radius $R_1$ of between 6 mm and =7.7 mm. Inner rows 81 and 84 have a cross-sectional radius $R_2$ of 13.5 mm. In turn, outer rows 81 and 85 have a cross-sectional radius $R_3$ of 27.5 mm. These dimensions result in the center row being focused at a range of 12 mm, the inner rows having a second focus at a range of 27 mm, and the outer rows having a third focus at 55 mm. Other dimensions and radii of curvature are possible.

One of the benefits afforded by a multi-focal offset concave lens, is that the cross-sectional depth and offset of the rows can be specifically adjusted to eliminate beam-splitting, discussed earlier. A concave lens with properly sized rows delivers all components of a received echo to the beamformer simultaneously, reducing or avoiding any problems with improperly delayed pulses. In calculating the cross-sectional depth and offset of each row of the lens, the azimuthal curvature of the lens, the desired focal zones, the number of rows, and the propagation speed are all taken into account. The result is an enhanced solution that greatly improves focusing and accuracy of the concave transducer array.

Beamformer

In system 40, a beamformer 41 combines return echoes received by a transducer to create a "scan line." A scan line is a representation of the strength of all echoes (or a lack thereof) received in response to a transmitted pulse in a single direction. The beamformer 41 first receives signals from nearby reflecting objects, and complements already received data with new return echoes. The data for portions of the scan line, and subsequently data for the entire scan line is stored temporarily or permanently in memory. Once a scan line has been assembled, the beamformer 41, along with the entire system, proceeds to assemble the next scan line.

In the field of ultrasound machines, a channel is an independent signal pathway between a transducer 52 and the beamformer 41. In one embodiment, the system 40 has 64 channels, even though the transducer array 52 has 320 elements in each of the 5 rows. This is made possible by a multiplexing structure 90 discussed below.

Multiplexing Structure

Once a return echo has been received by the transducer 52 and converted into usable form, it is sent to the beamformer 41 so that a scan line can be assembled. However, in an array that has multiple rows with multiple elements per row, the number of active elements and rows changes depending on the settings. In particular, inner and outer rows are activated to move the array's focal point further away from the array. Alternatively, for a focal point relatively close to the array, there is no need to activate the inner and outer rows, and a single center row suffices.

Figure 9A:
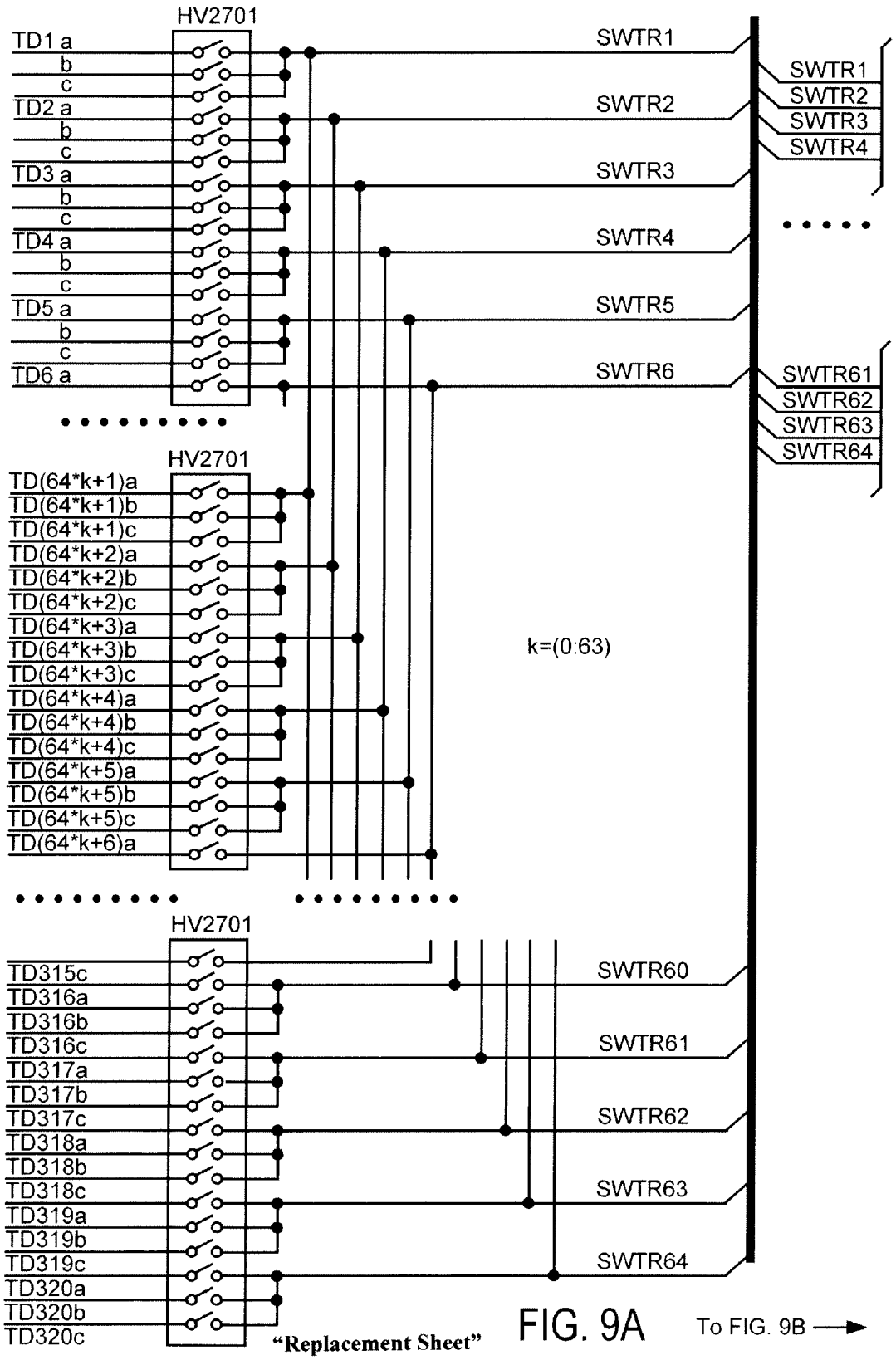
FIGS. 9A-9C are a detailed schematic of a multiplexing structure used with a concave transducer array, according to some embodiments.
Figure 9B:
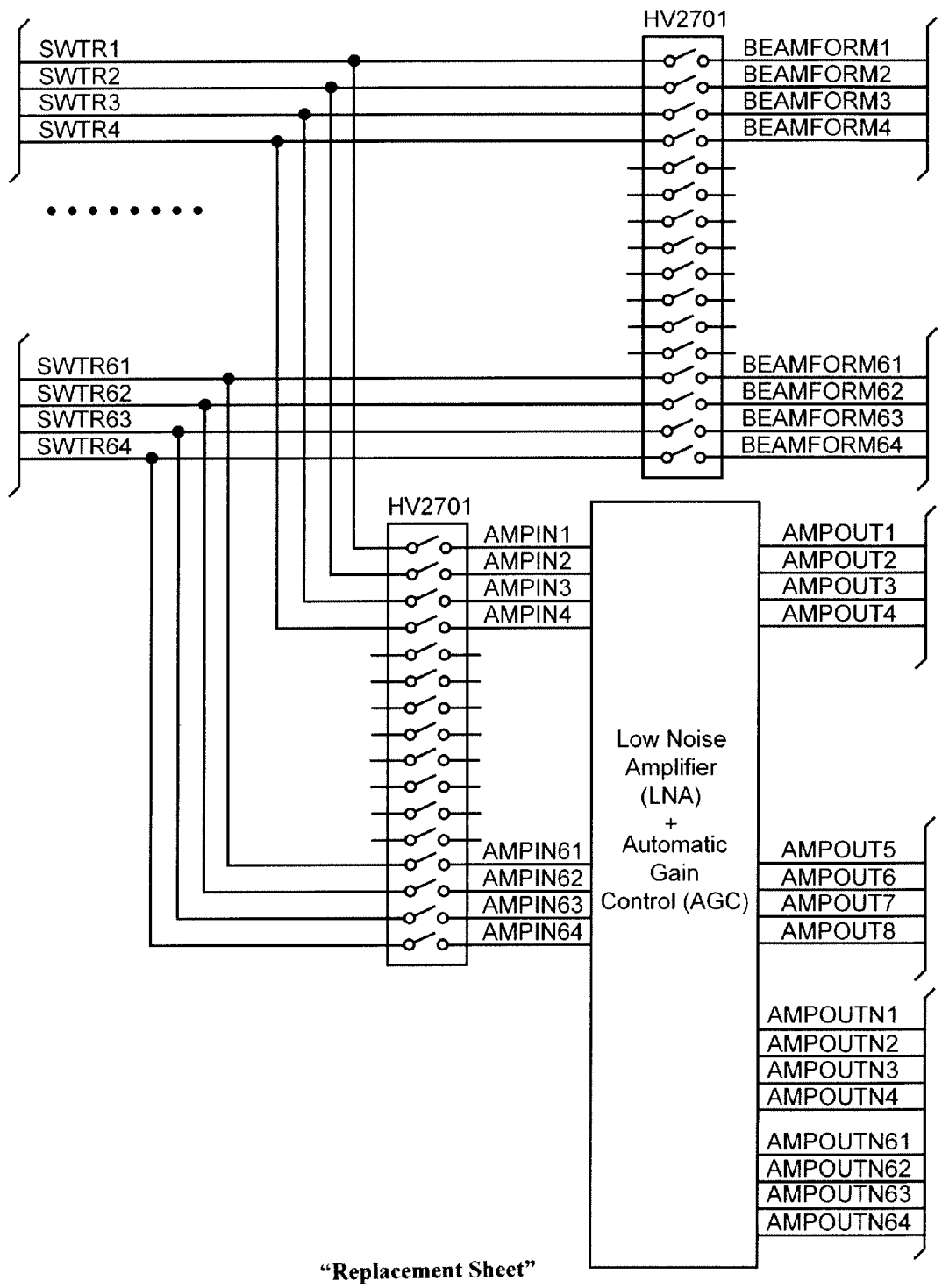
Figure 9C:
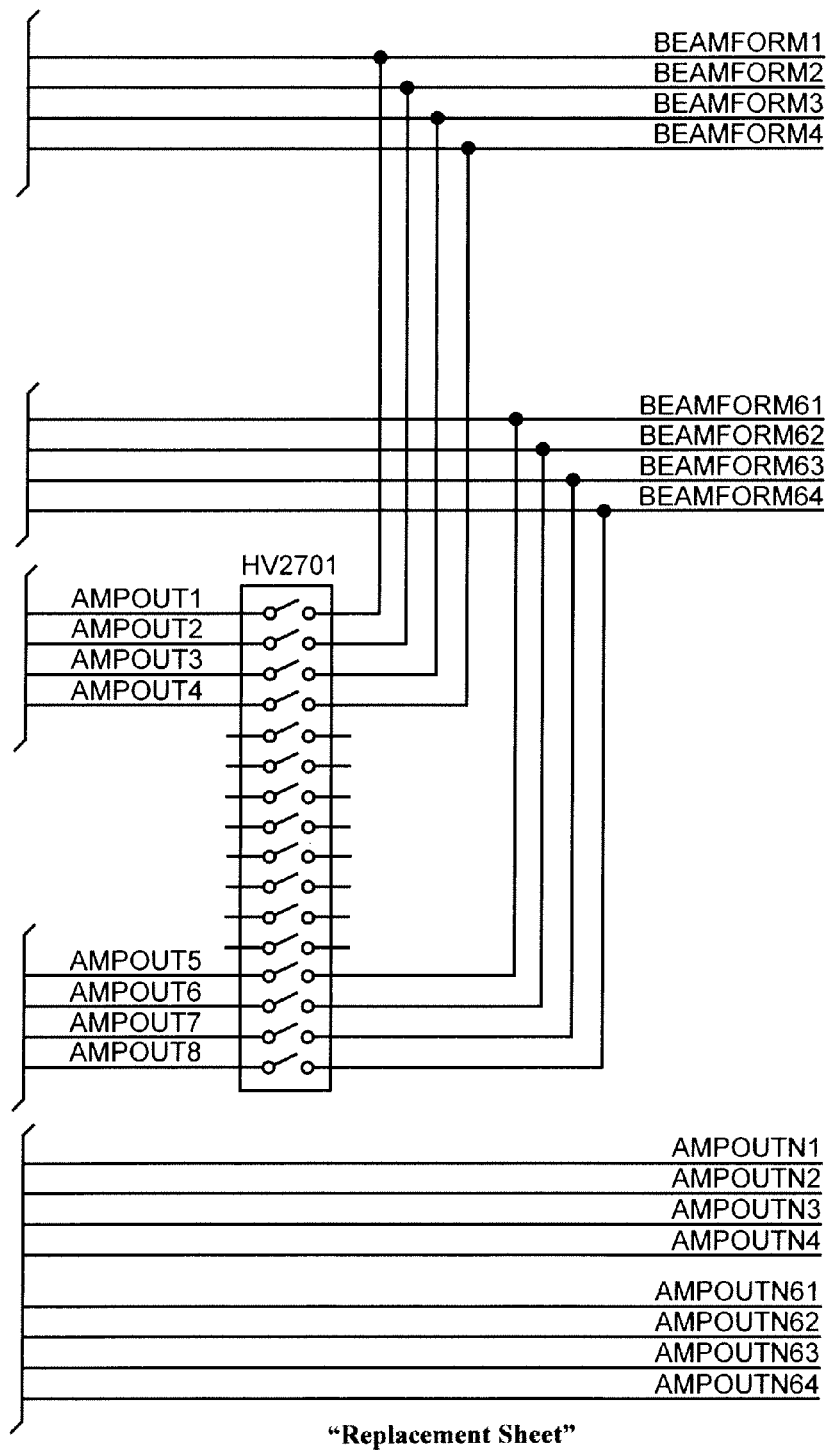

FIGS. 9A-9C are a schematic diagram of one embodiment of the multiplexing structure 90 employed by the concave 1.5D array described above. It will be understood by those of ordinary skill in the art that this multiplexing structure 90 is not limited to 64 channels, a total of 320 transducer elements per row, or 3 connections from the elevation standpoint. Adding extra channels, connections or transducers is a logical outgrowth of this multiplexing structure. At the same time, the number of channels, connections or transducers can be reduced to accommodate changing requirements.

The general function of the multiplexing structure 90 is to switch between the different transducers connected to the channels of beamformer 41. As mentioned earlier, one embodiment of the system 40 requires switching between 320×3 transducer connections and 64 beamformer 41 channels. The number of beamformer channels determines the maximum number of connections that can be active at one time. However, since connections of corresponding transducers from different inner (or outer) rows are tied together as explained earlier, e.g., a selected transducer from inner row 71 is tied to a selected transducer from inner row 72, it is possible to connect more than 64 transducers to the beamformer 41 at one time. In fact, if all rows are active, the maximum number of transducers connected to the beamformer is the Number of Beamformer Channels multiplied by the Number of Active Rows. Again, in one embodiment, the maximum number of active transducers that can be connected to the beamformer 41 is 64 Channels multiplied by 5 Rows totaling 320 Transducers. However, as the beamformer 41 itself only has 64 channels, the beamformer 41 sees a maximum of 64 signals at one time.

As described in the following section, a three-dimensional image includes a number of two-dimensional image slices created by the system 41. The following is a description of how the multiplexing structure functions during the creation of a single image slice, according to some embodiments.

Before the array 52 begins transmitting and receiving pulses, the operator selects the desired image settings. In some embodiments, the operator selects (1) the number of scan lines in the image, (2) the number of focal zones along each scan line, and (3) the depth of each focal zone. In other embodiments, one or more of the parameters, or all of the parameters, are automatically selected by system 40.

The system then proceeds in accordance with the following algorithm:

---

For each scan line
    For each focal zone (length)
        Select azimuthal (in-plane) aperture size based on current focal length
        Select number of rows based on current focal length
        Transmit pulse and listen for echoes
    Next focal zone
Next line

---

In order to enhance the depth of penetration and focus, in many embodiments all rows of the array are utilized. While inner and outer rows can be connected and disconnected depending on the depth of focus, in some embodiments the center row is substantially always connected to the multiplexing structure when that particular section of the array is active.

In some exemplary embodiments, the system 40 is capable of producing 320 or 640 lines per image slice, depending on the settings selected by the operator. To produce 320 lines, the system uses every column of elements, since there are 320 transducer elements in each row. Producing 640 scan lines is slightly more involved, but results in greater resolution.

Figure 12:
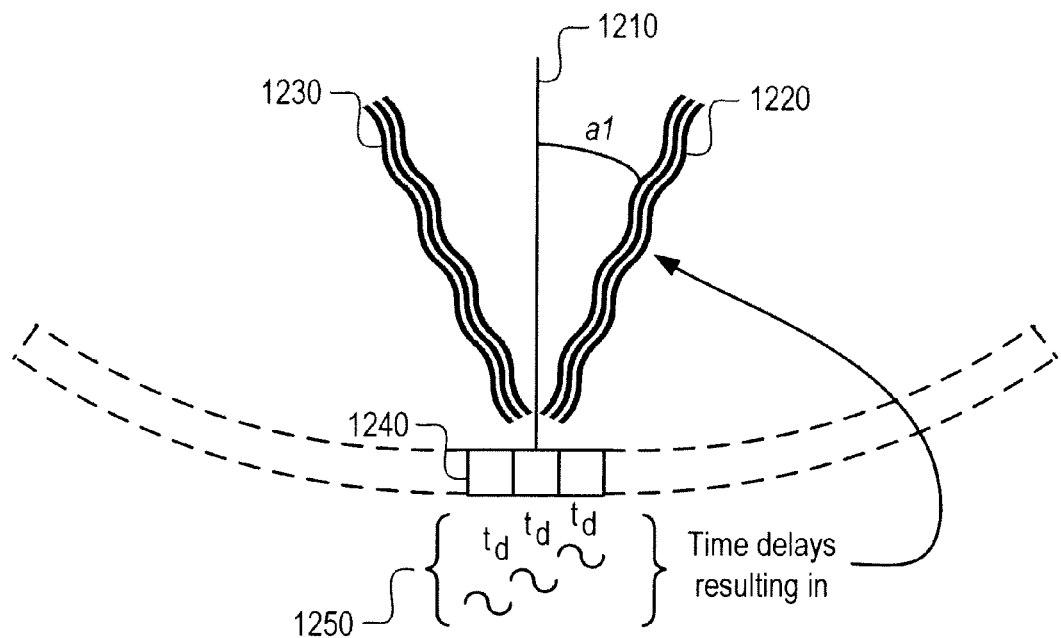
FIG. 12 is an illustration of micro-steering by a concave array, according to some embodiments.

One approach to gathering 640 scan lines by using only 320 elements is called micro-steering, illustrated in FIG. 12. In micro-steering, the system 40 selects the size of azimuthal aperture 1240, and transmits a pulse 1220 at angle a1 away from center line 1210. As in regular steering, different time delays 1250 applied to aperture 1240 determine angle a1 of the pulse. The system 40 then waits for a return echo from the same direction as the transmitted pulse. Next, the system 40 sends out pulse 1230 at the same angle a1 away from center line 1210, but this time on the opposite side of the center line, and waits to receive an echo from the same direction as the transmitted pulse. Since there are a total of 320 elements per row in the preferred embodiment of the transducer array, transmitting two pulses per element results in 640 total scan lines.

In another embodiment, the transducer array 52 gathers 640 scan lines from 320 elements by moving the transmit/receive apertures, and thereby creating additional scan-lines. The array 52 still receives 320 regular scan lines from the 320 elements. However, in between collecting the "regular" scan lines, the array creates a scan line that appears to be positioned directly between the two "regular" scan lines. This is done by shifting the active aperture laterally after the aperture has transmitted, and receiving the return echo on the shifted aperture. The reflections received by the shifted aperture are summed to create a scan line that appears to be positioned directly between the two adjacent scan lines.

Figure 13:
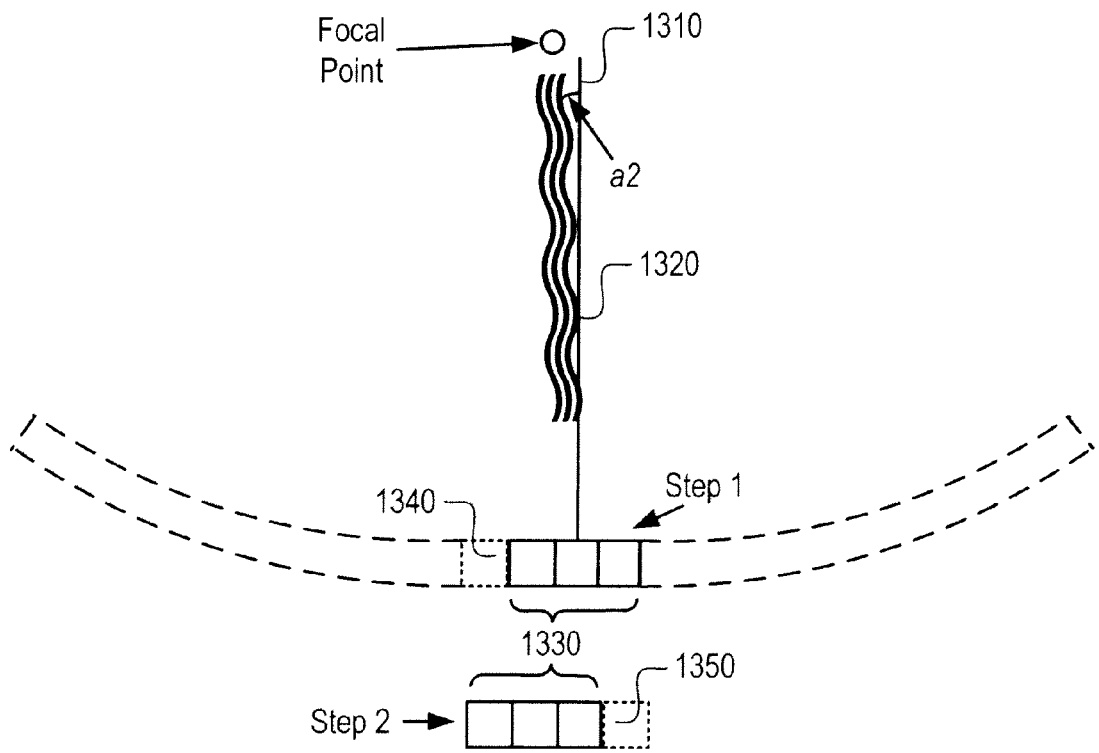
FIG. 13 is an illustration of compound imaging by a concave array, according to some embodiments.

In some embodiments, the system also reduces speckle by performing compound imaging, illustrated in FIG. 13. In ultrasound imaging, speckle is random noise caused by constructive or destructive interference. One way to eliminate random noise is to perform the same scan twice, from different directions. In Step 1 of compound imaging, the system 40 selects the azimuthal size of aperture 1330, and transmits pulse 1320 at a slight angle a2 from "center line" 1310 (here, the term center line refers to the normal at the center of the active aperture). The transducer array 52 receives the return echo from the same position, and subsequently shifts azimuthal aperture 1330 laterally by one or more elements, depicted as elements 1340 and 1350 in the figure. In Step 2, the shifted aperture transmits and receives a pulse toward the same focal point as in Step 1, but now the pulse is transmitted from a slightly different direction. Thus, the system receives two return echoes—one in Step 1, and another in Step 2. Angle a2 at which the pulse is transmitted should be sufficiently small, so that the return echoes in Step 1 look substantially similar to return echoes in Step 2. This process is repeated for different focal points, until two scan lines are collected, taking into account slight variations in the transmit/receive angle caused by a moving focal point. When data values for the two scan lines are averaged together, the random noise (speckle) is reduced, and the end result is a single scan line of greater quality. Both compound imaging and micro-steering can be performed simultaneously. While using both techniques takes more time, the benefits are immeasurable when a high quality image of suspect tissue (such as a tumor) is required.

In some embodiments, the system 40 also has advanced functionality, such as Power Doppler and/or Harmonic Tissue Imaging. In Power Doppler, the imaging system 40 takes advantage of the Doppler Effect to measure the flow and frequency of liquids moving inside the object being imaged. The Doppler Effect occurs when a transmitted wave is reflected by a moving object. If the reflector is moving closer to the transmitter/receiver, the reflected wave is of a higher frequency than the one initially transmitted toward the reflector. If the reflector is moving away from the transmitter/receiver, the reflected wave is of a lower frequency than the one initially transmitted toward the reflector. In the context of an ultrasound machine, this allows the processor to compare frequencies of the transmitted and received pulses, thereby detecting fluid flow inside the object being imaged. In the preferred embodiment, the system can detect blood and other fluid flow.

Harmonic Tissue Imaging can greatly increase the lateral resolution of ultrasound images. In one embodiment, the imaging system uses a band-pass filter to select one or more harmonic frequencies to transmit. This results in a narrower beam, which improves lateral resolution.

Transmit/Receive

The multiplexer 90 is illustrated in detail in FIGS. 9A-9C. One of the benefits of such a multiplexing structure 90 is that both rows and columns can be switched on and off in response to a desired configuration. In FIGS. 9A-9C, lines labeled TD1a-c...TD320a-c represent the transducer connections. Since the inner rows are tied together, and so are the outer rows, lines TD1a-TD320c in FIGS. 9A-9C correspond to lines TD1-320a-c in FIG. 7C. Lines BEAMFORM1...BEAMFORM64 represent the connections to each of the beamformer's channels. As previously mentioned, in one embodiment, the beamformer has 64 channels.

In operation, if all 5 rows are transmitting and receiving, the multiplexer 90 closes switches TDXa-c (where X stands for the column number of the firing transducer). If 3 rows are transmitting and receiving, the multiplexer closes switches TDXa-b only. In one embodiment, center row 70 can be turned off while the outer rows 71, 72, 73, and/or 74 are transmitting, resulting in excellent near-field resolution.

Once the array 52 receives the return echoes, the beamformer 41 sums the signals and the system 40 is ready to process the next scan line. The process is then repeated until all scan lines have been assembled.

One useful feature of such a multiplexing structure 90 is that both rows and transducer columns can be independently turned on and off. Adding this kind of multiplexing ability to a concave transducer array 52 permits the imaging system 40 to take full advantage of the concave array's properties, such as better focusing and depth of penetration. Thus, the imaging system 40 with a multiplexing structure 90 such as illustrated in FIGS. 9A-9C is very flexible when compared to other types of systems.

Another useful feature of the embodiment illustrated in FIGS. 9A-9C, is that the multiplexing structure 90 is also connected to the Low Noise Amplifier (LNA) and Automatic Gain Control (AGC) 42. This allows the multiplexer 90 to activate the LNA and AGC 42 as necessary to amplify or compensate a signal. It should be noted that when the LNA and AGC is engaged, lines SWTR1...SWTR64, which ordinarily connect transducers to the beamformer 41, are disconnected from BEAMFORM1...BEAMFORM64 to allow the return echoes to pass through the LNA and AGC. In contrast, when the array 52 is transmitting, the LNA and AGC are disconnected from the transmit path, to avoid noise and damage to the circuit.

Figure 14:
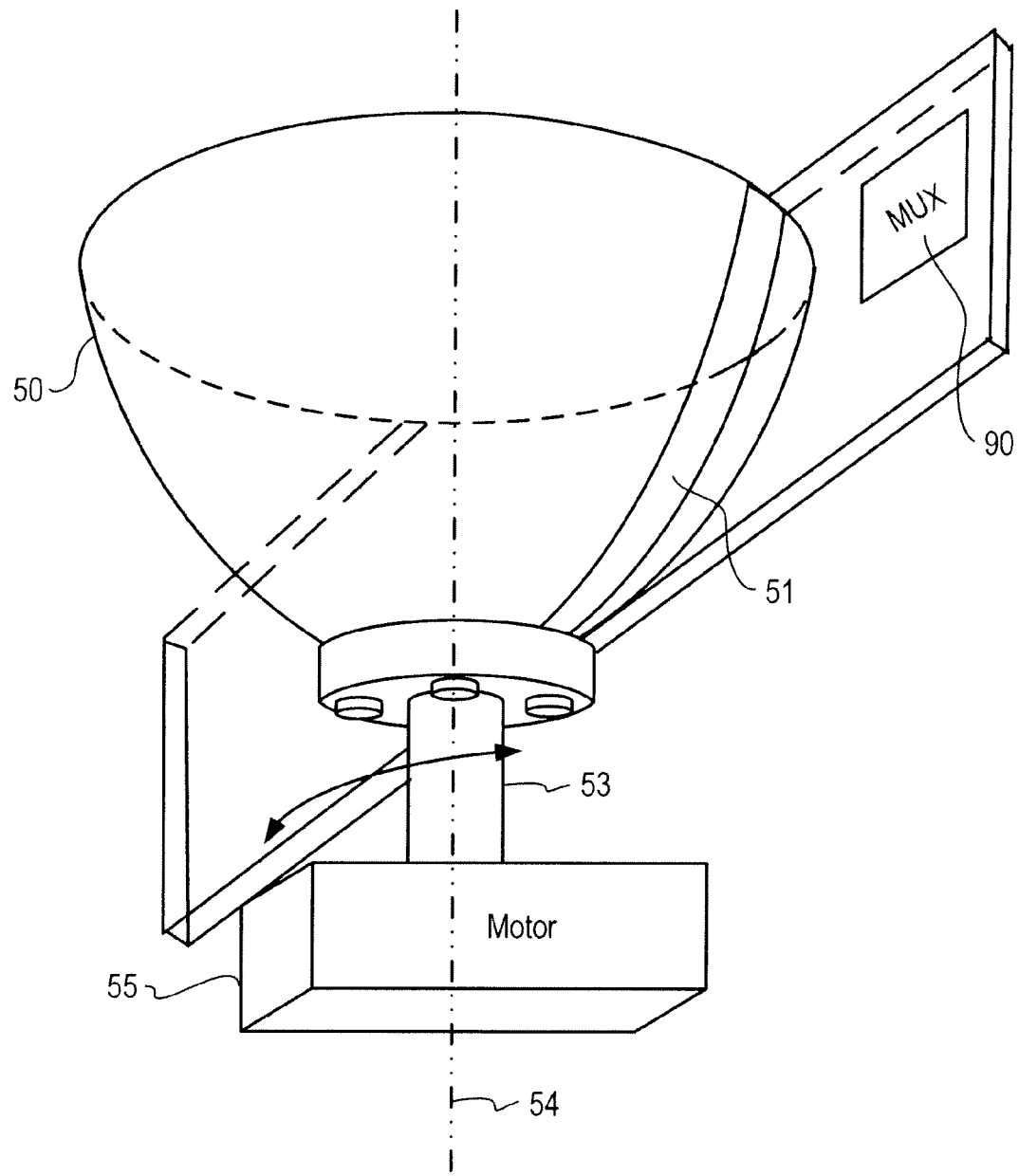
FIG. 14 is an illustration of a multiplexer and amplifier circuit board attached to a transceiver mounted on a dome, according to some embodiments.

As mentioned earlier, long signal pathways between a transducer and the beamformer 41 may degrade the quality of the signal as it attenuates and noise is introduced. To decrease signal degradation, short signal cables may be used. However, an even better approach is to mount the multiplexing structure (MUX) on the dome 50 and the transducer 52, as illustrated in FIG. 14. This approach permits the entire assembly (e.g., the dome 50, the array 52, the multiplexing structure 90, and the beamformer 41) to rotate together without sacrificing signal quality induced by having long signal pathways.

Processor

The processor 45 serves multiple roles, including receiving and processing user input, communicating with the beamformer 41, performing high level control of the rotation of motor 55, and storing the data gathered by the transducer 52 and beamformer 41 in a memory 46. The processor 45 may be specifically designed to perform these functions, or it may be a generic computer processor, such as one of the x86 family of Intel processors. In one embodiment, the processor 45 is a commercially available computer processor. It will be understood by those of ordinary skill in the art, that depending on the amount of data being processed and the architecture employed, even an ordinary microcontroller may satisfy some or all of the processor's roles. A different processor may be used to create the three-dimensional image from the plurality of image slices collected by the system.

Software

The software employed in the imaging system 40 can be written in many programming languages, provided that it retains certain core functionality. In one embodiment, software run by the processor 45 converts user input into a set of control commands for the rest of the system 40, including the motor 55, the beamformer 41, and the multiplexer 90. The same (or other) software may be used to generate the three-dimensional image from the plurality of collected image slices.

3D-Image Generation

Figure 1A:
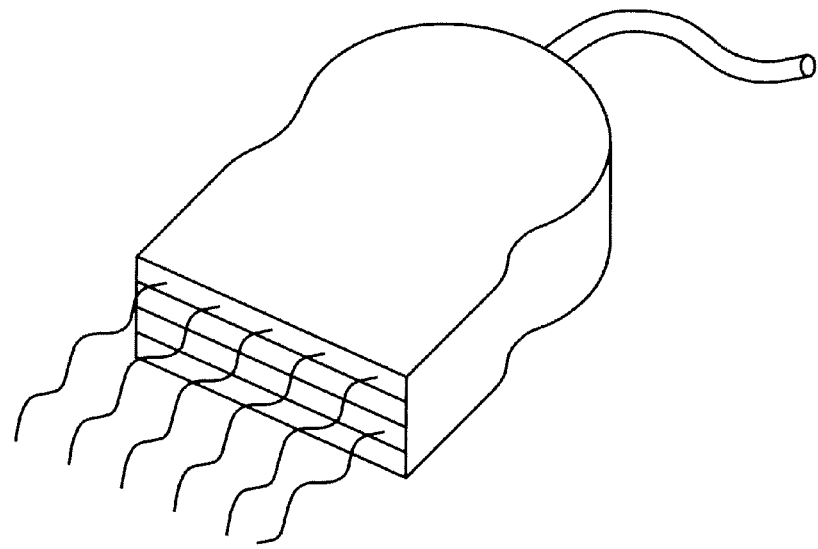
FIG. 1A is an illustration of a prior art hand-held ultrasonic scanner.
Figure 1B:
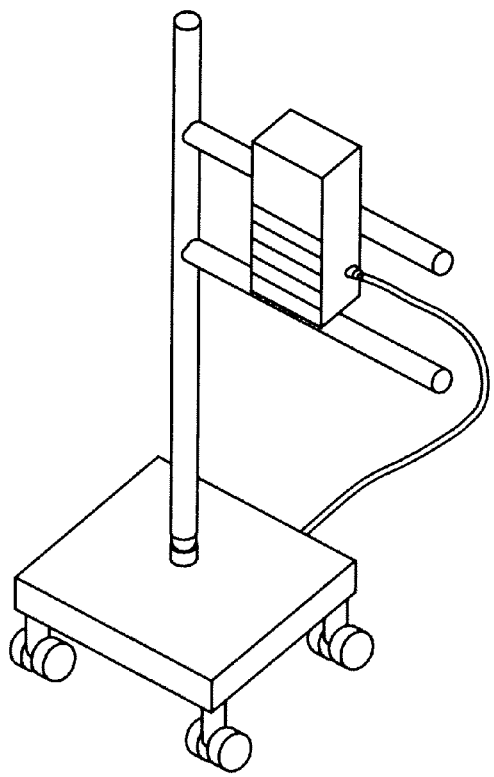
FIG. 1B is an illustration of a prior art stationary ultrasound machine.
Figure 2A:
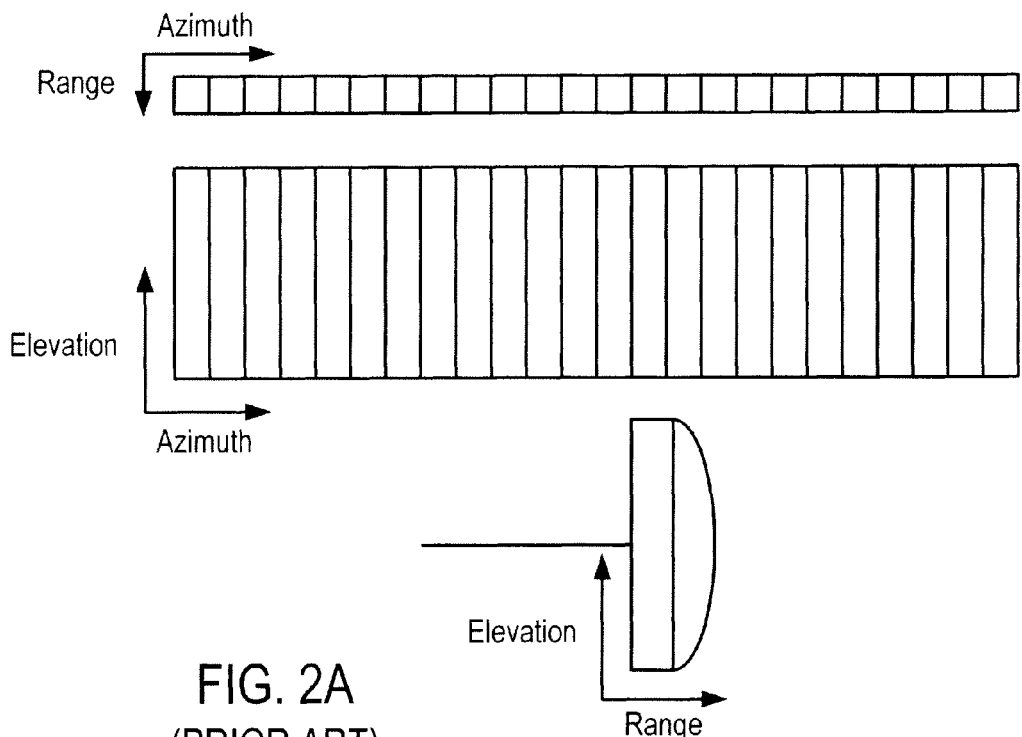
FIG. 2A is a diagram of a prior art 1D ultrasonic transducer array and lens.
Figure 2B:
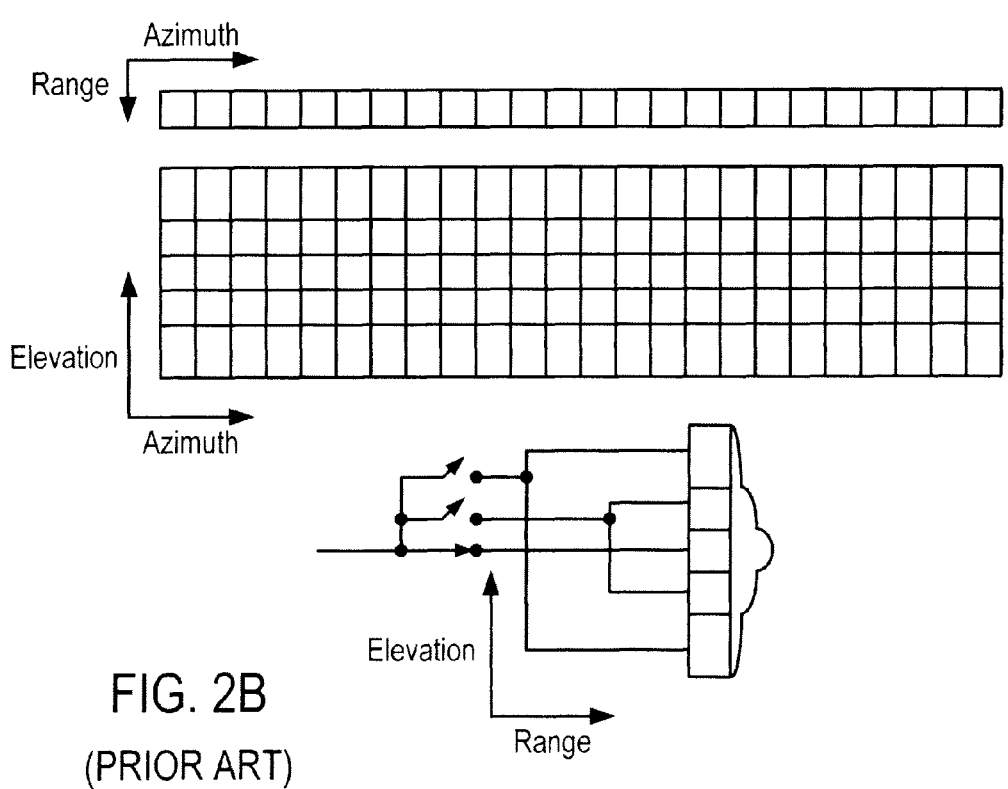
FIG. 2B is a diagram of a prior art 1.5D ultrasonic transducer array and lens.
Figure 3:
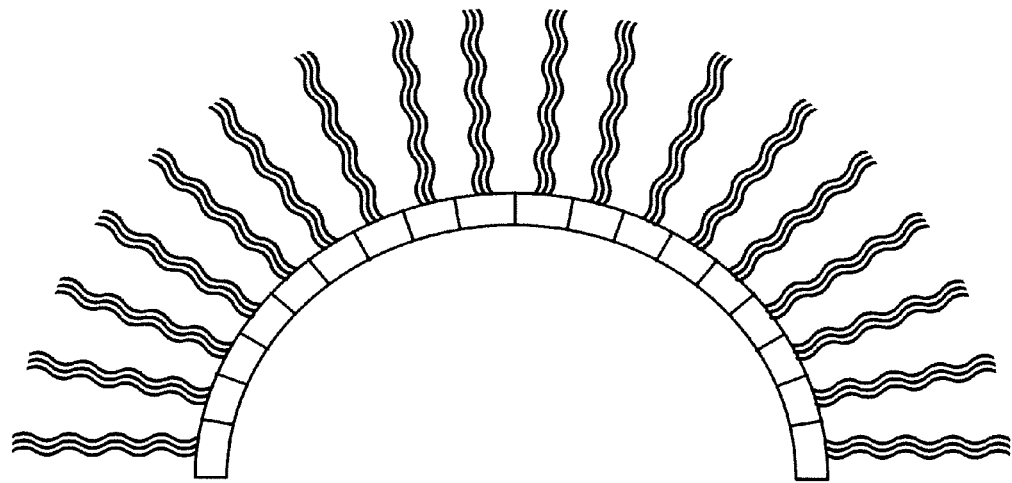
FIG. 3 is a diagram of a prior art 1D convex ultrasonic transducer array.
Figure 10:
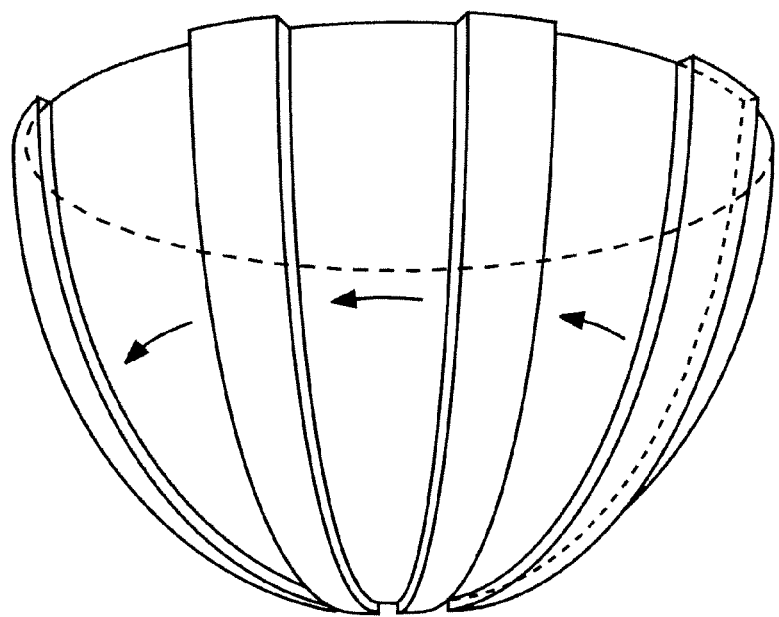
FIG. 10 is an illustration of a dome and the concave transducer array rotating synchronously around an axis, according to some embodiments.
Figure 11:
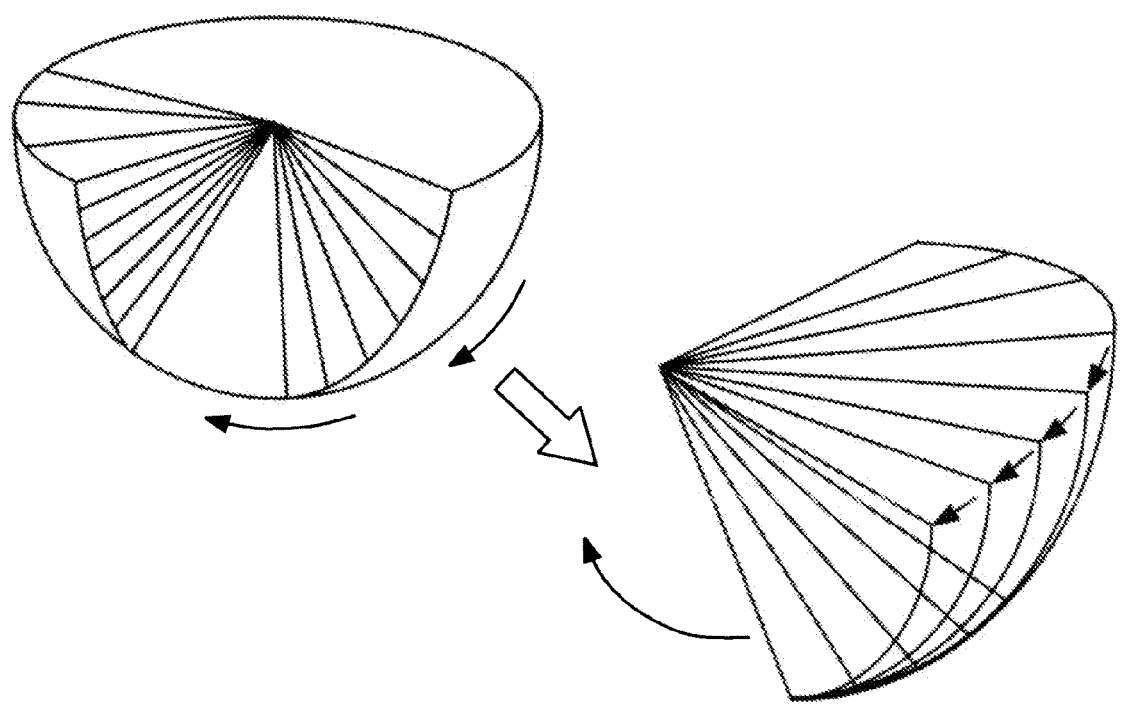
FIG. 11 is an illustration of a 3D image being reconstructed from a plurality of 2D image slices, according to some embodiments.

When the beamformer 41 has collected all of the return echoes, and the first image slice has been stored in memory 46, motor 55 rotates the dome 50 and array 52 by a single increment. In some embodiments, the system can vary the number of degrees by which the motor rotates the dome in a single increment. A schematic illustration of the revolving dome and array are illustrated in FIG. 10. The system 40 then creates and stores the next image slice, and stores the angle at which the slice was taken along with the image itself. This in some embodiments, this process is repeated until the dome 50 has gathered 360° of image slices as illustrated in FIG. 1. In one embodiment, the imaging system can rotate the dome by angular increments of 0.45°, 0.9°, or 1.8°, resulting in 800, 400, and 200 image slices respectively, after the dome has completed 360° of rotation. It will be understood by those of ordinary skill in the art that the dome does not have to complete a full revolution, i.e., need not turn 360°, to gather enough image slices for a three-dimensional representation. Even a modest rotation can be enough to gather enough image slices for a three-dimensional rendering of the scanned volume. The object located inside the dome may be considered "fully imaged" if the dome 50 makes one full revolution while gathering image slices.

At this point, the processor 45 combines all of the individual image slices to create a 3D representation of the contents of the dome 50. Naturally, a 3D representation including 800 image slices is more detailed than a 3D representation including 200 image slices. At the same time, a greater number of image slices requires more time to gather the slices. To accommodate various imaging needs, the system 40 can vary the number of image slices that it will gather based on default settings or user input. To eliminate or minimize the effect created by gaps that may appear between adjacent image slices, various image processing techniques, such as interpolation, can be used to "fill-in" the gaps occurring between adjacent image slices. In some embodiments, the operator can also select a desired image depth at which the processor 45 should begin displaying the 3D model on display 49. Depth variation can be beneficial because the person examining the 3D model may only be interested in what occurs at a specific depth, not the entire view of the dome's contents.

Freestanding Ultrasonic Breast Scanning Systems

In certain embodiments, the systems described herein are implemented as a freestanding ultrasonic breast scanning system that can provide automated whole breast imaging. Such freestanding systems can significantly improve detection of early-stage cancers in dense breast tissue as compared to mammography with no ionizing radiation exposure, no breast compression, and consistent reproducible images.

Figure 15:
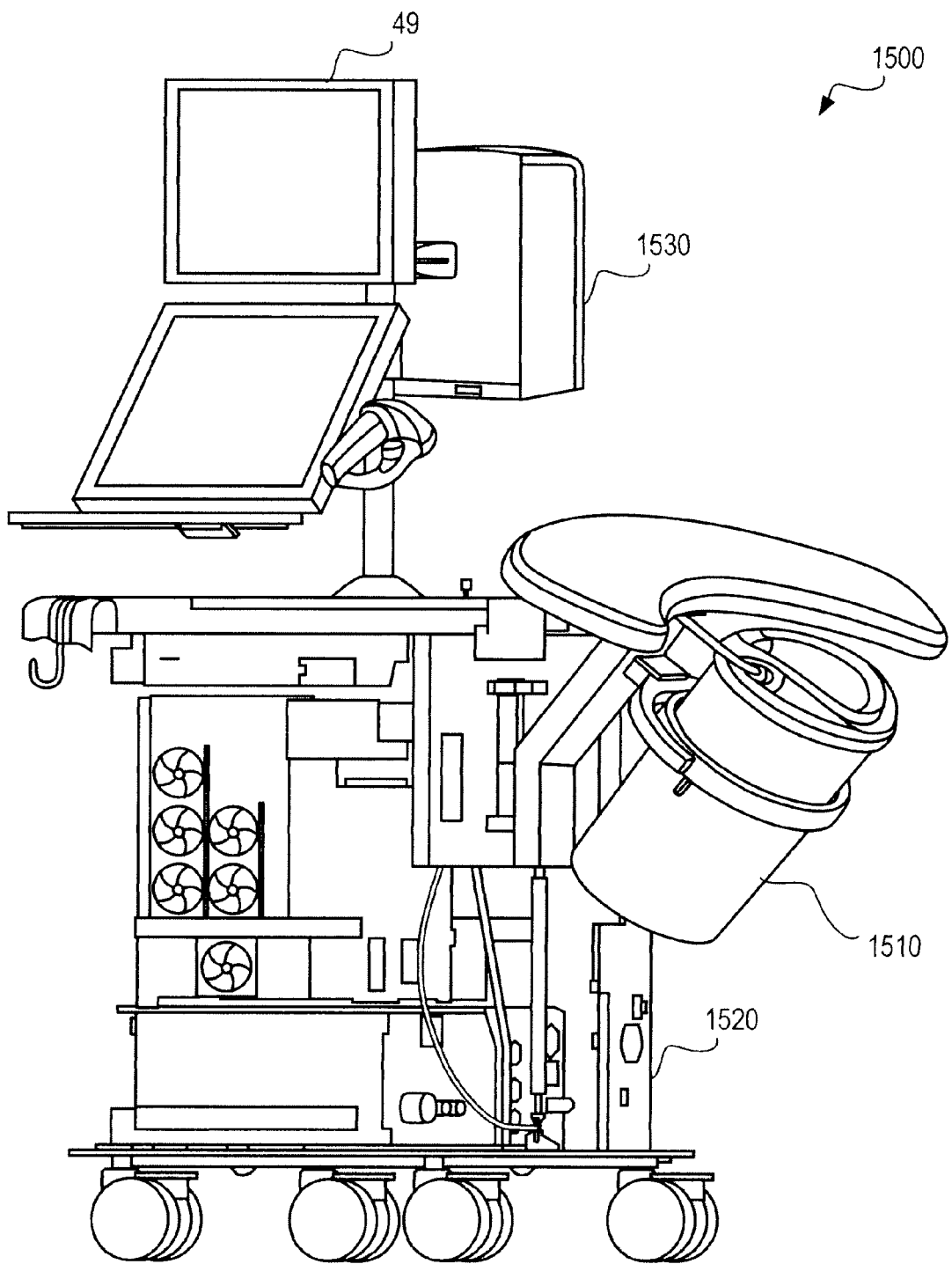
FIG. 15 is an illustration of a free-standing ultrasonic breast imaging system, according to some embodiments.

The system can be designed with modular components for ease of service. FIG. 15 shows an embodiment of a modular, freestanding system design. Additionally, the system can also be ergonomically designed, also as shown in FIG. 15. In certain embodiments described herein the systems are fully-automated, 3D breast tomography systems that can rapidly scan the entire breast without operator intervention, can produce an anatomically correct 3D image of the entire breast and can complete automated scanning of both breasts in less time than is currently required using manual ultrasound.

As illustrated in FIG. 15, in one embodiment a freestanding system 1500 includes a probe assembly 1510, a control subsystem 1520, and a clinical review workstation 1530 including display 49, which optionally includes touch-screen interface technology. The probe assembly 1510 includes a dome 50, transducer 52, and lens 80, which are not shown in FIG. 15 but can be configured as described above and as illustrated in FIGS. 4-14. The probe assembly 1510 also includes an outer housing (which can be, e.g., cylindrical) into which the dome, transducer, and lens assembly fits. The control subsystem 1520 includes processor 45 and amplifier and gain control 42. Multiplexer 90 and beamformer 41 can be part of the dome assembly within probe assembly 1510 as is illustrated in FIG. 14, or can be part of the control subsystem 1520 and in operable communication with probe assembly 1510. In certain embodiments, the automated probe assembly 1510 is capable of generating images at high frame rates and collecting hundreds of images per breast, as described above with reference to FIGS. 4-14. The system 1500 can also include a linear transducer for manual breast image acquisition (not shown).

Figure 16:
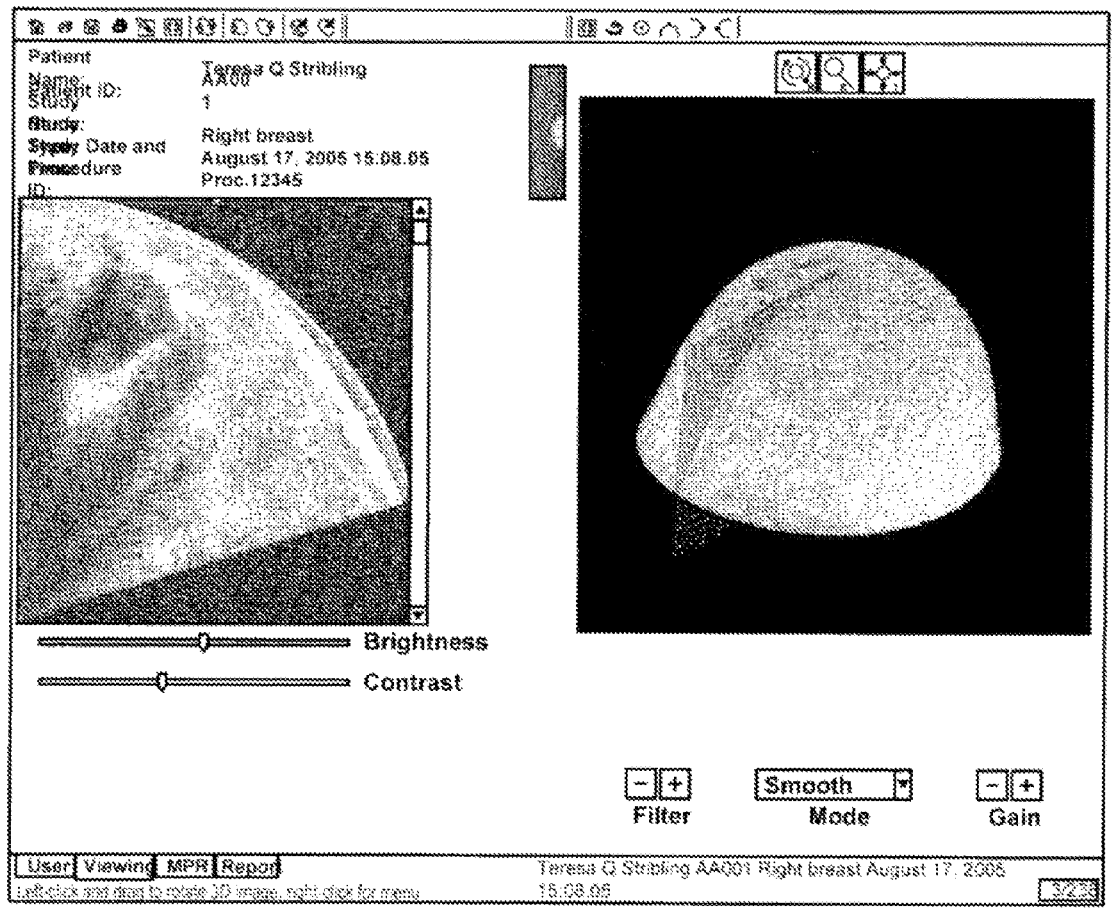
FIG. 16 is an example of an image produced by an FFDU system, according to some embodiments.

The system's 3D clinical review workstation 1530 presents renderings of 3D ultrasonic data obtained by probe assembly 1510 and control subsystem 1520. FIG. 16 shows an exemplary image produced by the system's 3D clinical review workstation 1530. The workstation 1530 can include a 3D visualization environment, computer aided detection, 200, 400 or 800 frame data acquisition, DICOM/PACS compliant, digital archiving capable, image Segmentation and/or multiplanar visualization, thus allowing a radiologist or other operator to readily review ultrasonic images for a patient, and optionally other information about the patient that is stored on workstation 1530.

Features that can be included in various embodiments of the system 1500 include one or more of: enhanced diagnostic accuracy, state of the art interpretation software (2D and 3D capabilities), and state of the art enhanced user-interface; image segmentation that offers crisp, clear images of the region of interest for improved visualization of breast tissue; multiplanar visualization that provides a flexible multiplanar display using the 3D volume to enable image display in any orthogonal plane; separate 3D clinical review workstation that can reside either on-site or off-site, allowing for remote diagnosis; financial efficiencies such as significant reductions in diagnostic costs, and potential significant incremental reimbursement revenues per patient when compared to manual ultrasound.

Figure 17:
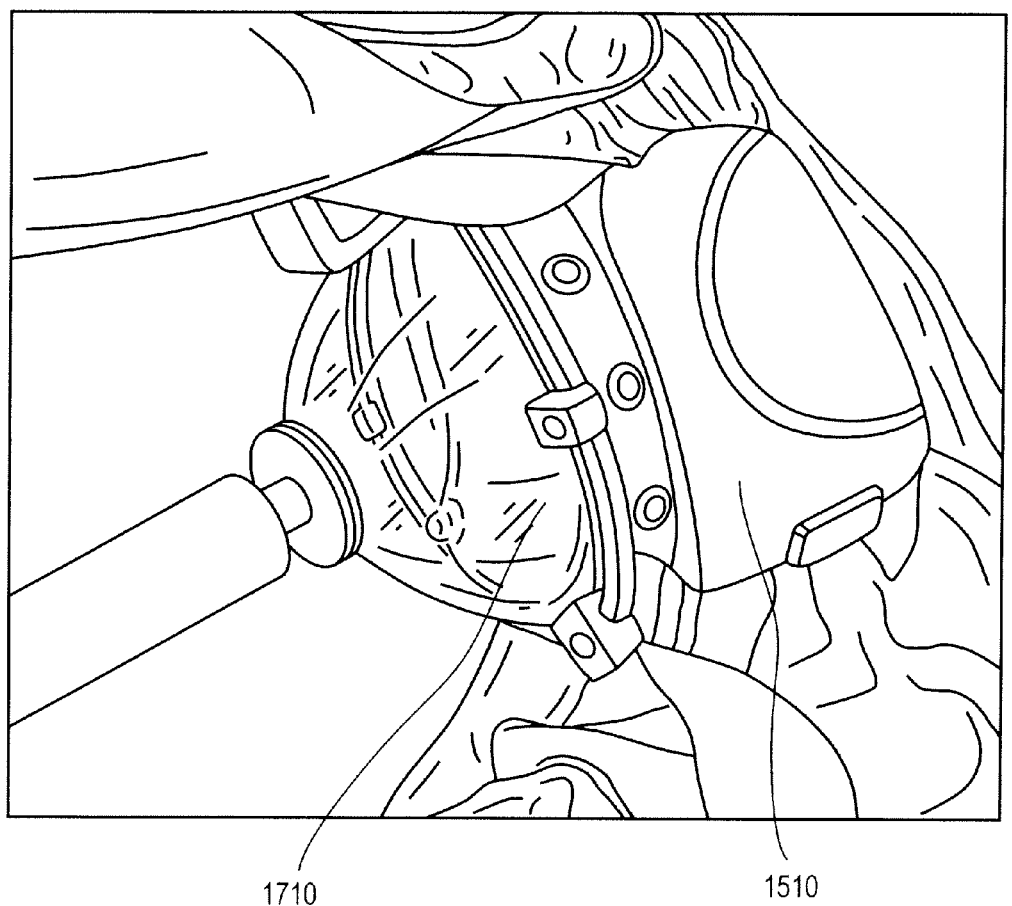
FIG. 17 is an illustration of another embodiment of an FFDU system.

In some embodiments, system 1500 is configured to enable standardized positioning for patients, thus enhancing the ability to obtain consistent, reproducible images. For example, FIG. 17 illustrates an embodiment of a probe assembly 1510 that is configured to accept a breast 1710 that can be any of a wide variety of sizes and/or have many different types of characteristics, e.g. breasts of young women, dense breast tissue, or augmented breasts.

Figure 18:
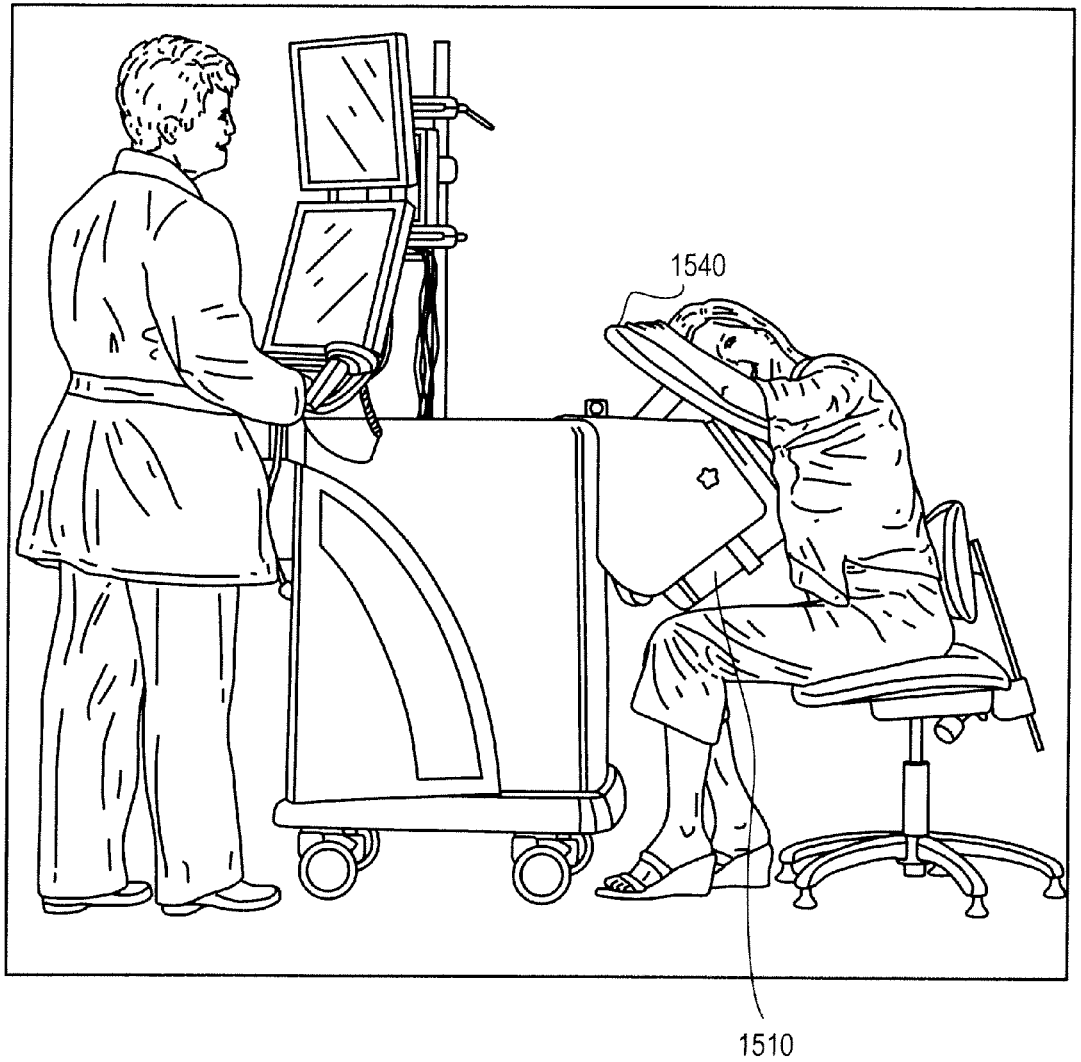
FIG. 18 is an illustration of an FFDU system used in conjunction with a coupling gel, according to some embodiments.

In some embodiments, system 1500 can be used with a coupling medium (e.g., a gel or other suitable medium) and are configured for a comfortable scanning position for the patient. As illustrated in FIG. 18, the probe assembly 1510 is angled so that the breast of the patient is pendulous or semi-pendulous, and the patient can rest her arm on arm rest 1540 which can allow for improved imaging of the entirety of the breast and reduce compression of the breast. A heated coupling medium is used to fill voids between tissue and scanner, create a warm comforting experience, and accommodate various breast sizes. Suitable gels also do not compress the breast and leave breast in a "natural" state. The combination of such systems and gels can reduce the variations in diagnostic inaccuracies associated with manual ultrasound systems. For further details on coupling media, see PCT/US08/08414, the entire contents of which are incorporated herein by reference.

Additionally, in certain embodiments system 1500 also includes an integrated biopsy port (not illustrated).

Exemplary Embodiments

In accordance with some embodiments, an ultrasound system and method are provided for producing a three-dimensional representation of an object being examined. In particular, the system includes a concave 1.5D transducer array, a multi-focal lens structure, a multiplexing structure, and a beamformer.

In one embodiment, a concave multi-row transducer array and a multiplexing structure provide a more efficient approach to beam focusing by increasing the available transmit aperture, thereby increasing the depth of penetration and decreasing the number of required beamformer channels. In addition, the multiplexing structure and concave array can vary the array's f-number without increasing the number of beamformer channels.

In another embodiment, a concave multi-row transducer array and compound focusing lens further narrow the beam and avoid splitting of pulses.

In another embodiment, a dome with a concave transducer array mounted over a slit in the dome rotate around the dome's axis and create image slices of the object located inside the dome.

In another embodiment, a multiplexing structure is mounted on the dome along with the array to reduce signal degradation caused by long signal pathways.

In another embodiment, the system collects and stores image slices taking during its rotation. After a desired number of image slices have been stored, the system assembles a 3D representation of the object located inside the dome by combining the stored image slices.

In another embodiment, an ultrasound imaging system is provided including: a dome; a motor for rotating the dome; a concave ultrasonic transducer array mounted on the dome; a concave lens attached to the concave ultrasonic transducer array; and a multiplexing circuit connected to the concave ultrasonic transducer array.

In another embodiment, an ultrasound imaging system is provided including: a dome; a motor for rotating the dome; a concave ultrasonic transducer array mounted on the dome; a concave lens attached to the concave ultrasonic transducer array; and a multiplexing circuit connected to the concave ultrasonic transducer array, wherein the motor is a stepper motor.

In another embodiment, an ultrasound imaging system is provided including: a dome; a motor for rotating the dome; a concave ultrasonic transducer array mounted on the dome; a concave lens attached to the concave ultrasonic transducer array; a multiplexing circuit connected to the concave ultrasonic transducer array; and a low-noise amplifier.

In another embodiment, an ultrasound imaging system is provided including: a dome; a motor for rotating the dome; a concave ultrasonic transducer array mounted on the dome; a concave lens attached to the concave ultrasonic transducer array; a multiplexing circuit connected to the concave ultrasonic transducer array; a low-noise amplifier; and an automatic gain controller.

In another embodiment, an ultrasound imaging system is provided including: a dome; a motor for rotating the dome; a concave ultrasonic transducer array mounted on the dome; a concave lens attached to the concave ultrasonic transducer array; a multiplexing circuit connected to the concave ultrasonic transducer array; a low-noise amplifier; and an automatic gain controller, wherein the low-noise amplifier and the automatic gain controller are connected to the multiplexing circuit.

In another embodiment, an ultrasound imaging system is provided including: a dome; a motor for rotating the dome; a concave ultrasonic transducer array mounted on the dome; a concave lens attached to the concave ultrasonic transducer array; and a multiplexing circuit connected to the concave ultrasonic transducer array, wherein the multiplexing circuit is mounted on the dome.

In another embodiment, an ultrasound imaging system is provided including: a dome; a motor for rotating the dome; a concave ultrasonic transducer array mounted on the dome; a concave lens attached to the concave ultrasonic transducer array; a multiplexing circuit connected to the concave ultrasonic transducer array; and a processor for creating a three-dimensional image from scan patterns collected during the dome's rotation.

In another embodiment, a concave ultrasonic transducer array is provided, including: a plurality of curvilinear rows, wherein each row includes at least one ultrasonic transducer element; a concave multi-focus lens attached to the transmitting and receiving face of the concave ultrasonic transducer array.

In another embodiment, a concave ultrasonic transducer array is provided, including: a plurality of curvilinear rows, wherein each row includes at least one ultrasonic transducer element; a concave multi-focus lens attached to the transmitting and receiving face of the concave ultrasonic transducer array; and a multiplexing circuit connected to the concave ultrasonic transducer array.

In another embodiment, a concave ultrasonic transducer array is provided, including: a plurality of curvilinear rows, wherein each row includes at least one ultrasonic transducer element; a concave multi-focus lens attached to the transmitting and receiving face of the concave ultrasonic transducer array; a multiplexing circuit connected to the concave ultrasonic transducer array; and an amplifier and an automatic gain controller connected to the multiplexing circuit.

In another embodiment, a concave ultrasonic transducer array is provided, including: a plurality of curvilinear rows, wherein each row includes at least one ultrasonic transducer element; a concave multi-focus tens attached to the transmitting and receiving face of the concave ultrasonic transducer array; a multiplexing circuit connected to the concave ultrasonic transducer array; an amplifier and an automatic gain controller connected to the multiplexing circuit; and a beamformer connected to the multiplexing circuit.

In another embodiment, a concave ultrasonic transducer array is provided, including: a plurality of curvilinear rows, wherein each row includes at least one ultrasonic transducer element; a concave multi-focus lens attached to the transmitting and receiving face of the concave ultrasonic transducer array, wherein each row includes 320 transducer elements.

In another embodiment, a concave ultrasonic transducer array is provided, including: a plurality of curvilinear rows, wherein each row includes at least one ultrasonic transducer element; a concave multi-focus lens attached to the transmitting and receiving face of the concave ultrasonic transducer array, wherein each row includes 480 transducer elements.

In another embodiment, a concave multi-focus acoustic lens is provided, including: a plurality of concave rows, wherein only rows symmetric in elevation along the azimuthal centerline of the lens have the same focal points, and wherein each concave row is offset from other rows in the range direction to prevent gaps in focusing coverage.

In another embodiment, a concave multi-focus acoustic lens is provided, including: a plurality of concave rows, wherein only rows symmetric in elevation along the azimuthal centerline of the lens have the same focal points, and wherein each concave row is offset from other rows in the range direction to prevent gaps in focusing coverage, wherein the lens is made of silicone.

In another embodiment, a concave multi-focus acoustic lens is provided, including: a plurality of concave rows, wherein only rows symmetric in elevation along the azimuthal centerline of the lens have the same focal points, and wherein each concave row is offset from other rows in the range direction to prevent gaps in focusing coverage, wherein the lens is made of urethane.

In another embodiment, a method for multiplexing signals received by a concave multi-row transducer array between the concave multi-row transducer array and a beamformer is provided, including: turning on transducer rows based on a desired elevational beam performance; turning on transducer columns based on a desired azimuthal beam performance; connecting transducer rows and columns to the beamformer.

In another embodiment, a method for multiplexing signals received by a concave multi-row transducer array between the concave multi-row transducer array and a beamformer is provided, including: turning on transducer rows based on a desired elevational beam performance; turning on transducer columns based on a desired azimuthal beam performance; connecting transducer rows and columns to the beamformer; and connecting transducer rows and columns to a low noise amplifier.

In another embodiment, a method for multiplexing signals received by a concave multi-row transducer array between the concave multi-row transducer array and a beamformer is provided, including: turning on transducer rows based on a desired elevational beam performance; turning on transducer columns based on a desired azimuthal beam performance; connecting transducer rows and columns to the beamformer; connecting transducer rows and columns to a low noise amplifier; and connecting transducer rows and columns to an automatic gain controller.

In another embodiment, a method for creating an image with a concave transducer array and multiplexer is provided, including: receiving user input for a desired number of scan lines; receiving user input for a desired number of focal zones; and determining a focal depth for each focal zone based on properties of the concave transducer array.

In another embodiment, a method for creating an image with a concave transducer array and multiplexer is provided, including: receiving user input for a desired number of scan lines; receiving user input for a desired number of focal zones; determining a focal depth for each focal zone based on properties of the concave transducer array; determining the size of a transmit and receive azimuthal aperture for each focal zone; determining the number of transmit and receive rows for each focal zone; transmitting an ultrasound pulse; and receiving a returned ultrasound echo.

In another embodiment, a method for creating an image with a concave transducer array and multiplexer is provided, including: receiving user input for a desired number of scan lines; receiving user input for a desired number of focal zones; determining a focal depth for each focal zone based on properties of the concave transducer array; determining the size of a transmit and receive azimuthal aperture for each focal zone; determining the number of transmit and receive rows for each focal zone; transmitting an ultrasound pulse; receiving a returned ultrasound echo; and amplifying a returned ultrasound echo.

In another embodiment, a method for creating a three-dimensional image with a concave transducer array mounted on a dome having a polar axis is provided, including: creating a plurality of image slices with a concave transducer array mounted on a dome rotating around its polar axis; and assembling a three-dimensional image from the plurality of image slices created by the concave transducer array.

Under another aspect, three-dimensional ultrasound imaging systems provide automated whole breast imaging. Certain embodiments of the systems provided herein allow the radiologist or other operator to view an entire breast in a three-dimensional environment by using fully automated ultrasound acquisition and image analysis algorithms. Such embodiments can aid radiologists in determining if small stage-0 (DCIS) and early stage-1 cancer is present in the 30-40% of breast screening patients who have dense breast tissue. Such embodiments can provide cancer detection in patients with dense breast tissue, and their adoption in the breast diagnostic environment may result in the earlier detection of breast cancer, in most cases, prior to its metastasis, resulting in greater survival rates and decreased therapeutic costs.

Although various embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A multi-focus acoustic lens for focusing ultrasonic pulses transmitted by a concave transducer array at desired locations in an object, the concave transducer array having a multiplicity of individual concave transducer rows for generating multiple images of the object in a range and azimuthal direction, comprising:
   (a) a multiplicity of lens rows forming an entire lens comprised of a center lens row and a plurality of uncentered lens rows forming at least two outer lens rows relative the said center lens row when said entire lens is viewed elevationally,
   wherein each said lens row has an inner surface and an outer surface,
   wherein each said outer surface is configured to form a convex shape in the azimuthal direction,
   wherein each said inner surface is configured to form a concave arcuate surface in the azimuthal direction,
   wherein, each said lens row is elevationally and azimuthally aligned to cover an entire transmit/receive area of a respective individual concave transducer row to focus a beam transmitted through the said entire lens in an elevational and azimuthal direction,
   wherein, when a pair of said uncentered lens rows are symmetric in an elevation direction with respect to an azimuthal centerline of the said center lens rows, said uncentered lens row pair has a same focal range,
   wherein the said inner surface of each of said lens rows varies in height in a range direction relative to a lens row of the entire lens to which it is adjacent,
   wherein said each lens row has a constant curvature and a radius when viewed cross-sectionally,
   wherein the said center lens row has a smaller radius and a larger curvature in size as compared to each of the said radius and each of the said curvature of each said uncentered lens row, so that a center portion of the said center lens row is not coincident with a center portion of an arc formed by any symmetric uncentered lens row pair,
   wherein the said lens rows have f-numbers which are essentially constant with one another,
   wherein each said lens row is sized to simultaneously deliver all components of an echo received by the entire lens to a beamformer; and
   (b) a moving mechanism operably coupled to the entire lens for moving the entire lens to one or more radial positions with respect to the object being imaged thereby generating the multiple images in the range and azimuthal direction.

2. The multi-focus acoustic lens of claim 1, wherein at least a subset of the lens rows have a different lateral dimension than other of the lens rows.

3. The multi-focus lens of claim 1, wherein each of the lens rows comprises a material having a speed of propagation for a sound wave of less than 1.5 mm/μs.

4. The multi-focus acoustic lens of claim 3, wherein the material comprises one of silicone or urethane.

5. The multi-focus acoustic lens of claim 1, further comprising N lens rows, wherein N is an odd integer greater than or equal to 3.

6. The multi-focus acoustic lens of claim 5, wherein N=5.

7. The multi-focus acoustic lens of claim 1, wherein the multi-focus acoustic lens is for focusing transmitted ultrasonic pulses to desired locations in an object and for focusing ultrasonic pulses from the desired locations.

8. The multi-focus acoustic lens of claim 1, wherein the multiplicity of rows forms a unitary structure.

9. The multi-focus acoustic lens of claim 1, wherein the multiplicity of rows are formed using a unitary structure.

10. A multi-focus acoustic lens for focusing ultrasonic pulses transmitted by a concave transducer array having transducer rows at desired locations in an object for generating multiple images of the object in an azimuthal direction, comprising:
- a body member that includes a front surface, said body member having an inner surface, the inner surface being configured and arranged so to be concave in the azimuthal direction;
- wherein the body member front surface is configured and arranged so to that a multiplicity of lens rows are provided therein, the multiplicity of lens rows forming an entire lens comprised of a center lens row, and a plurality of uncentered lens rows forming at least two outer lens rows relative to the said center lens row when said entire lens is viewed elevationally, where each of the multiplicity of lens rows has an outer surface, the outer surface being convex in the azimuthal direction;
- wherein a pair of uncentered lens rows that are symmetric in an elevation direction with respect to an azimuthal centerline of said center lens of the body member have same focal points;
- wherein each said lens row is elevationally and azimuthally aligned to cover an entire transmit/receive area of a respective individual concave transducer row to focus a beam transmitted through the entire lens in an elevational and azimuthal direction;
- wherein said inner surface of each said lens rows varies in height in a range direction relative to a lens row of the entire lens to which it is adjacent;
- wherein each said lens row has a constant curvature and a radius when viewed cross-sectionally;
- wherein the said center lens row has a smaller radius and a larger curvature in size as compared to each of the said radius and each of the said curvature of each said uncentered lens rows, so that a center portion of the said center lens row is not coincident with a center portion of an arc formed by any symmetric uncentered lens row pair;
- wherein the said lens rows have f-numbers which are essentially constant with one another;
- wherein each said lens row is sized to simultaneously deliver all components of an echo received by the entire lens to a beamformer; and
- a moving mechanism operably coupled to the body member for moving the body member including the entire lens to one or more radial positions with respect to the object being imaged thereby generating the multiple images in the azimuthal direction.

11. The multi-focus acoustic lens of claim 10, wherein at least a subset of the lens rows have a different lateral dimension than other of the lens rows.

12. The multi-focus lens of claim 10, wherein each of the lens rows comprises a material having a speed of propagation for a sound wave of less than 1.5 mm/µs.

13. The multi-focus acoustic lens of claim 12, wherein the material comprises one of silicone or urethane.

14. The multi-focus acoustic lens of claim 10, further comprising N lens rows, wherein N is an odd integer greater than or equal to 3.

15. The multi-focus acoustic lens of claim 14, wherein N=5.

16. The multi-focus acoustic lens of claim 10, wherein the first and second directions are orthogonal to each other.

17. The multi-focus acoustic lens of claim 10, wherein the multi-focus acoustic lens is for focusing transmitted ultrasonic pulses to desired locations in an object and for focusing ultrasonic pulses from the desired locations.

18. A multi-focus lens for focusing transmitted ultrasonic signals at desired locations in an object and for focusing returned ultrasonic signals received from the object for generating multiple images of the object in an azimuthal direction, where the ultrasonic signals are transmitted from a concave ultrasound transducer array configured to transmit ultrasonic signals through the multi-focus lens for focusing the transmitted ultrasonic signals into an object, wherein the concave ultrasound transducer array includes a plurality of curvilinear concave-shaped transducer rows, wherein each curvilinear concave-shaped transducer row, which includes at least one ultrasonic transducer element, is of the same or different dimension as the other curvilinear concave-shaped transducer rows, said multi-focus lens comprising:
- multiple lens rows forming an entire lens comprised of a center lens row and a plurality of uncentered lens rows forming at least two outer lens rows relative to the center lens row when said entire lens is viewed elevationally for focusing the ultrasonic signals in an elevation direction, wherein each lens row is configured with an inner and outer surface;
- wherein the inner surface is of a concaved curved shape in the azimuthal direction for elevationally and azimuthally aligning with a corresponding transmit/receive area of a respective transducer row for covering the corresponding transducer row and the ultrasonic transducer element;
- wherein the outer surface for each lens row is of a convex shape in the azimuthal direction for focusing the concave ultrasound transducer array in an elevational direction at desired locations into an object along a path of the transmitted ultrasonic signals;
- wherein the concave inner surface of at least one inner surface of the lens row varies in height in a range direction relative to the concave inner surface of a lens row of the entire lens to which it is adjacent;
- wherein the concave inner surfaces of the uncentered lens rows that are symmetric in the elevation direction about an azimuthal centerline of the center row of the multiple lens rows are configured and arranged so as to have same focal points;
- wherein each said lens row has a constant curvature and a radius when viewed cross-sectionally,
- wherein the said center lens row has a smaller radius and a larger curvature in size as compared to each of the said radius and each of the said curvature of each said uncentered lens row, so that a center portion of the said center lens row is not coincident with a center portion of an arc formed by any symmetric uncentered lens row pair;
- wherein the said lens rows have f-numbers which are essential constant with one another;
- wherein each said lens row is sized to simultaneously deliver all components of an echo received by the entire lens to a beamformer; and
- a moving mechanism operably coupled to the entire lens when the multi-focus lens is aligned with the concave ultrasound transducer array for moving the multi-focus lens and the concave ultrasound transducer array to one or more radial positions with respect to the object to be imaged thereby generating the multiple images in the azimuthal direction.

19. The multi-focus lens of claim 18, wherein the transmitted ultrasonic signals are focused at a plurality of the one or more radial positions.

20. The multi-focus lens of claim 18, wherein the object to be imaged is selected from a group of objects, the group consisting of a shoulder, a breast, a wrist, an ankle, and an elbow.

21. The multi-focus lens of claim 18, wherein:
the object to be imaged is a breast; and
wherein the multiple lens sections and the concave ultrasound transducer array are aligned so as to image a volume of the breast.

22. The multi-focus lens of claim 18, further comprising N lens sections, wherein N is an odd integer greater than or equal to 3.

23. The multi-focus lens of claim 22, wherein N=5.

24. The multi-focus lens of claim 18, wherein the multiple lens sections forms a unitary structure.

25. The multi-focus lens of claim 18, wherein the multiple lens sections are formed using a unitary structure.

26. The multi-focus lens of claim 18, wherein the multi-focus lens focuses ultrasonic signals received from the desired locations in an object and wherein the outer surface for each lens section is for focusing the ultrasonic signals from the desired locations in the concave ultrasound transducer array.

27. A multi-focus lens for focusing ultrasonic pulses at desired locations in an object for generating multiple images of the object in an azimuthal direction when the ultrasonic pulses are transmitted from a concave ultrasound transducer array configured to transmit ultrasonic pulses into an object, wherein the concave ultrasound transducer array includes a plurality of curvilinear concave-shaped transducer rows, wherein each curvilinear concave-shaped transducer row, which includes at least one ultrasonic transducer element, is of the same or different dimension as the other curvilinear concave-shaped transducer rows, said multi-focus compound lens comprises:
multiple lens rows forming an entire lens comprised of a center lens row and a plurality of uncentered lens rows forming at least two outer lens rows relative to the center lens row when the entire lens is viewed elevationally for focusing ultrasonic pulses from a concave ultrasound transducer array in an elevation direction, wherein each said multiple lens row is configured with an inner surface and outer surface, wherein the inner surface is of a curvilinear concave-shape in the azimuthal direction for azimuthally aligning with a corresponding curvilinear concave-shaped transducer row for covering the transmit/receive area of the corresponding curvilinear concave-shaped transducer row and the ultrasonic transducer element associated therewith and the outer surface is of a convex elevation shape in the azimuthal direction for focusing the concave ultrasound transducer array in an elevation direction at desired locations into an object along a path of ultrasonic pulses when transmitted from a concave ultrasound transducer array in an elevation direction, wherein the inner surface of at least one lens row varies in height in a range direction relative to a lens row of the entire lens to which it is adjacent and wherein when, two or more of said uncentered multiple lens rows are symmetric in an elevation direction with respect to an azimuthal centerline of center lens row, said symmetric uncentered lens rows have the same focal points as one another; wherein each said lens row has a constant curvature and a radius when viewed cross-sectionally, wherein the said center lens row has a smaller radius and a larger curvature in size as compared to each of the said radius and each of the said curvature of each said uncentered lens row, so that a center portion of the said center lens row is not coincident with a center portion of an arc formed by any symmetric uncentered lens row, pair, wherein the said lens rows have f-numbers which are essentially constant with one another, and wherein each said lens row is sized to simultaneously deliver all components of an echo received by the entire lens to a beamformer; and a moving mechanism operably coupled to the entire lens when each of the multiple lens rows is azimuthally aligned with the corresponding curvilinear concave-shaped transducer row, for moving the entire lens and the concave ultrasound transducer array to one or more radial positions with respect to the object to be imaged thereby generating the multiple images in the azimuthal direction.

28. The multi-focus lens of claim 27, wherein the multi-focus lens focuses ultrasonic pulses received from the desired locations in an object and wherein the outer surface for each lens section is for focusing the ultrasonic pulses from the desired locations in the concave ultrasound transducer array.

* * * * *